(12) United States Patent
Hioki

(10) Patent No.: US 12,421,563 B2
(45) Date of Patent: Sep. 23, 2025

(54) LEATHER IMPROVING AGENT

(71) Applicant: Kao Corporation, Tokyo (JP)

(72) Inventor: Takahiro Hioki, Wakayama (JP)

(73) Assignee: Kao Corporation, Tokyo (JP)

( * ) Notice: Subject to any disclaimer, the term of this patent is extended or adjusted under 35 U.S.C. 154(b) by 465 days.

(21) Appl. No.: 17/768,311

(22) PCT Filed: Oct. 29, 2020

(86) PCT No.: PCT/JP2020/040704
§ 371 (c)(1),
(2) Date: Apr. 12, 2022

(87) PCT Pub. No.: WO2021/085563
PCT Pub. Date: May 6, 2021

(65) Prior Publication Data
US 2024/0117454 A1 Apr. 11, 2024

(30) Foreign Application Priority Data

Oct. 30, 2019 (JP) .................. 2019-197738

(51) Int. Cl.
C14C 1/08 (2006.01)
C12N 9/64 (2006.01)

(52) U.S. Cl.
CPC .............. C14C 1/08 (2013.01); C12N 9/6489 (2013.01)

(58) Field of Classification Search
CPC ................................ C14C 1/08; C12N 9/6489
USPC ......................................................... 8/94.18
See application file for complete search history.

(56) References Cited

U.S. PATENT DOCUMENTS

| | | | |
|---|---|---|---|
| 5,340,737 A * | 8/1994 | Siegler | C12N 9/6481 435/219 |
| 2003/0061666 A1 | 4/2003 | Covington | |
| 2010/0263134 A1 | 10/2010 | Covington | |
| 2021/0207116 A1 | 7/2021 | Hioki et al. | |

FOREIGN PATENT DOCUMENTS

| | | |
|---|---|---|
| CN | 1505686 A | 6/2004 |
| CN | 103060487 A | 4/2013 |
| CN | 105132600 A | 12/2015 |
| CN | 105524906 A | 4/2016 |
| EP | 4 239 071 A1 | 9/2023 |
| JP | 04-108387 A | 4/1992 |
| JP | 2004-043660 A | 2/2004 |
| JP | 2016-527876 A | 9/2016 |
| JP | 2019-122301 A | 7/2019 |
| JP | 2019-123803 A | 7/2019 |
| JP | 2022-073146 A | 5/2022 |
| WO | WO 01/35901 A2 | 5/2001 |
| WO | WO 02/088397 A1 | 11/2002 |
| WO | WO 2014/194117 A2 | 12/2014 |
| WO | WO 2019/142773 A1 | 7/2019 |

OTHER PUBLICATIONS

Zhao HL et al. Elastolytic mechanism of a novel M23 metalloprotease pseudoalterin from deep-sea *Pseudoalteromonas* sp. CF6-2: cleaving not only glycyl bonds in the hydrophobic regions but also peptide bonds in the hydrophilic regions involved in cross-linking. J Biol Chem. Nov. 16, 2012;287(47):39710-20. doi: 10.1074.*
Extended European Search Report (EESP) issued on Feb. 12, 2024 for European Patent Application No. 20881726.2, by the European Patent Office, Munich, Germany.
Sivaprakasam, S et al., "Calorimetric on-line monitoring of proteolytic activity of *P. aeruginosa* cultivated in a bench-scale biocalorimeter," Biochemical Engineering Journal 39 (Apr. 2008) 149-156.
International Search Report for PCT/JP2020/040704; I.A. fd Oct. 29, 2020), mailed Dec. 1, 2020, the Japan Patent Office, Tokyo, Japan.
International Preliminary Report on Patentability (IPRP), Chapter I of the Patent Cooperation Treaty, including the Written Opinion, for PCT/JP2020/040704; I.A. fd Oct. 29, 2020) issued May 3, 2022, by the International Bureau of WIPO, Geneva, Switzerland.

* cited by examiner

*Primary Examiner* — Amina S Khan
(74) *Attorney, Agent, or Firm* — Sterne, Kessler, Goldstein & Fox P.L.L.C.

(57) ABSTRACT

Provided are a leather improving agent which exhibits the effect of suppressing contraction of hide to enlarge the area; and a method for treating leather using the leather improving agent. The leather improving agent comprises an M23A subfamily protease as an active ingredient.

5 Claims, 3 Drawing Sheets

Specification includes a Sequence Listing.

SEQUENCE LISTING

<160> NUMBER OF SEQ ID NOS: 10

<210> SEQ ID NO 1
<211> LENGTH: 1134
<212> TYPE: DNA
<213> ORGANISM: Achromobacter lyticus
<220> FEATURE:
<221> NAME/KEY: sig_peptide
<222> LOCATION: (1)..(72)
<220> FEATURE:
<221> NAME/KEY: CDS
<222> LOCATION: (73)..(1131)
<220> FEATURE:
<221> NAME/KEY: mat_peptide
<222> LOCATION: (595)..(1131)

<400> SEQUENCE: 1

```
atgaaaaaaa tctcaaaagc tggtctggga ctggctctgg tctgtgctct ggcgacgatt      60
ggaggcaacg ca tct gct cag gga cat  gga tta agc ggc gaa  gat ctg       108
              Ser Ala Gln Gly His  Gly Leu Ser Gly Glu  Asp Leu
                       -170                    -165 gtt tac tct  tac gat gaa atg ttt  gat ttt gat atc gat  gcc tac        153
Val Tyr Ser  Tyr Asp Glu Met Phe  Asp Phe Asp Ile Asp  Ala Tyr
        -160                 -155                  -150 ctg gca aaa  cat gcg ccg cat ctg  cat aaa cat agc gaa  gaa atc        198
Leu Ala Lys  His Ala Pro His Leu  His Lys His Ser Glu  Glu Ile
        -145                 -140                  -135 tct cat tgg  gcc gga tat tct ggc  att tca ccg aaa gtt  ctt atc        243
Ser His Trp  Ala Gly Tyr Ser Gly  Ile Ser Pro Lys Val  Leu Ile
        -130                 -125                  -120 gca tta atg  gaa caa cag tca gga  gct gtg agc gcc aaa  aga gca        288
Ala Leu Met  Glu Gln Gln Ser Gly  Ala Val Ser Ala Lys  Arg Ala
        -115                 -110                  -105 aca aat cgc  ccg ttt ggc aaa ctt  gcc aga gca gat gga  ttt ggc gcc    336
Thr Asn Arg  Pro Phe Gly Lys Leu  Ala Arg Ala Asp Gly  Phe Gly Ala
        -100                  -95                   -90 caa aca cgc  gaa gtg gcg tta gct  ctg aga gaa tct ctt  tat gaa cgc    384
Gln Thr Arg  Glu Val Ala Leu Ala  Leu Arg Glu Ser Leu  Tyr Glu Arg
         -85                  -80                   -75 gat ccg gat  gga gcc aaa ggc ccg  gtc aca tta gcc aga  gca aac ccg    432
Asp Pro Asp  Gly Ala Lys Gly Pro  Val Thr Leu Ala Arg  Ala Asn Pro
-70                       -65                   -60                -55 ctg cag gca  ctt ttt gaa cgc tca  gga gat aat gaa ccg  gca gcg gct    480
Leu Gln Ala  Leu Phe Glu Arg Ser  Gly Asp Asn Glu Pro  Ala Ala Ala
                    -50                  -45                   -40 tta aga gga  gat ggc gaa ttt caa  ctt gtc tac ggc aga  tta ttt aac    528
Leu Arg Gly  Asp Gly Glu Phe Gln  Leu Val Tyr Gly Arg  Leu Phe Asn
         -35                  -30                   -25 gaa ccg cgc  cag gca aaa gcc gca  agc gat aga ttt gcg  aaa gct gga    576
Glu Pro Arg  Gln Ala Lys Ala Ala  Ser Asp Arg Phe Ala  Lys Ala Gly
         -20                  -15                   -10 ccg gat gtt  caa ccg tta tct ccg  aat gga ctg ctt cag  ttt ccg ttt    624
Pro Asp Val  Gln Pro Leu Ser Pro  Asn Gly Leu Leu Gln  Phe Pro Phe
          -5                   -1 1                5                 10 ccg aga ggc  gca tct tgg cat gtg  ggc gga gct cat aca  aac aca gga    672
Pro Arg Gly  Ala Ser Trp His Val  Gly Gly Ala His Thr  Asn Thr Gly
                     15                   20                   25 tca ggc aat  tat ccg atg tca agc  ctg gat atg tca aga  ggc gga ggc    720
Ser Gly Asn  Tyr Pro Met Ser Ser  Leu Asp Met Ser Arg  Gly Gly Gly
                     30                   35                   40 tgg gga agc  aat caa aac ggc aat  tgg gtt tca gcg agc  gcg gct gga    768
Trp Gly Ser  Asn Gln Asn Gly Asn  Trp Val Ser Ala Ser  Ala Ala Gly
```

```
                45                  50                  55
tct ttt aaa cgc cat tct tca tgc ttt gct gaa att gtt cat aca ggc    816
Ser Phe Lys Arg His Ser Ser Cys Phe Ala Glu Ile Val His Thr Gly
     60                  65                  70 ggc tgg tca aca aca tac tac cat ctg atg aac atc cag tac aat aca    864
Gly Trp Ser Thr Thr Tyr Tyr His Leu Met Asn Ile Gln Tyr Asn Thr
 75                  80                  85                  90 ggc gcg aac gtt agc atg aat aca gcc atc gca aac ccg gct aat aca    912
Gly Ala Asn Val Ser Met Asn Thr Ala Ile Ala Asn Pro Ala Asn Thr
                 95                 100                 105 caa gcg cag gct ctg tgc aac gga ggc caa agc aca gga ccg cat gaa    960
Gln Ala Gln Ala Leu Cys Asn Gly Gly Gln Ser Thr Gly Pro His Glu
            110                 115                 120 cat tgg tca ctg aaa cag aac ggc tca ttt tac cat ctg aac gga aca   1008
His Trp Ser Leu Lys Gln Asn Gly Ser Phe Tyr His Leu Asn Gly Thr
        125                 130                 135 tac ctt tca ggc tat aga atc aca gcg aca ggc agc tct tat gat aca   1056
Tyr Leu Ser Gly Tyr Arg Ile Thr Ala Thr Gly Ser Ser Tyr Asp Thr
    140                 145                 150 aat tgt agc cgc ttt tat ttg aca aaa aat gga cag aac tac tgc tat   1104
Asn Cys Ser Arg Phe Tyr Leu Thr Lys Asn Gly Gln Asn Tyr Cys Tyr
155                 160                 165                 170 ggt tat tat gtg aat cct gga ccg aac taa                           1134
Gly Tyr Tyr Val Asn Pro Gly Pro Asn
                175
```

<210> SEQ ID NO 2
<211> LENGTH: 353
<212> TYPE: PRT
<213> ORGANISM: Achromobacter lyticus

<400> SEQUENCE: 2

```
Ser Ala Gln Gly His  Gly Leu Ser Gly Glu  Asp Leu Val Tyr Ser
                -170                -165                -160

Tyr Asp Glu Met Phe  Asp Phe Asp Ile Asp  Ala Tyr Leu Ala Lys
                -155                -150                -145

His Ala Pro His Leu  His Lys His Ser Glu  Glu Ile Ser His Trp
                -140                -135                -130

Ala Gly Tyr Ser Gly  Ile Ser Pro Lys Val  Leu Ile Ala Leu Met
                -125                -120                -115

Glu Gln Gln Ser Gly  Ala Val Ser Ala Lys  Arg Ala Thr Asn Arg
                -110                -105                -100

Pro Phe Gly Lys Leu  Ala Arg Ala Asp Gly  Phe Gly Ala Gln Thr Arg
            -95                  -90                  -85

Glu Val Ala Leu Ala  Leu Arg Glu Ser Leu  Tyr Glu Arg Asp Pro Asp
            -80                   -75                  -70

Gly Ala Lys Gly Pro  Val Thr Leu Ala Arg  Ala Asn Pro Leu Gln Ala
         -65                     -60                   -55

Leu Phe Glu Arg Ser  Gly Asp Asn Glu Pro  Ala Ala Leu Arg Gly
        -50                     -45                  -40

Asp Gly Glu Phe Gln  Leu Val Tyr Gly Arg  Leu Phe Asn Glu Pro Arg
-35                      -30                  -25                  -20

Gln Ala Lys Ala Ala  Ser Asp Arg Phe Ala  Lys Ala Gly Pro Asp Val
                -15                  -10                   -5

Gln Pro Leu Ser Pro  Asn Gly Leu Leu Gln  Phe Pro Phe Pro Arg Gly
         -1  1                   5                       10

Ala Ser Trp His Val  Gly Gly Ala His Thr  Asn Thr Gly Ser Gly Asn
```

```
              15                  20                  25
Tyr Pro Met Ser Ser Leu Asp Met Ser Arg Gly Gly Trp Gly Ser
 30                  35                  40                  45

Asn Gln Asn Gly Asn Trp Val Ser Ala Ser Ala Gly Ser Phe Lys
                 50                  55                  60

Arg His Ser Ser Cys Phe Ala Glu Ile Val His Thr Gly Trp Ser
                     65                  70                  75

Thr Thr Tyr Tyr His Leu Met Asn Ile Gln Tyr Asn Thr Gly Ala Asn
                 80                  85                  90

Val Ser Met Asn Thr Ala Ile Ala Asn Pro Ala Asn Thr Gln Ala Gln
 95                 100                 105

Ala Leu Cys Asn Gly Gly Gln Ser Thr Gly Pro His Glu His Trp Ser
110                 115                 120                 125

Leu Lys Gln Asn Gly Ser Phe Tyr His Leu Asn Gly Thr Tyr Leu Ser
                130                 135                 140

Gly Tyr Arg Ile Thr Ala Thr Gly Ser Ser Tyr Asp Thr Asn Cys Ser
                145                 150                 155

Arg Phe Tyr Leu Thr Lys Asn Gly Gln Asn Tyr Cys Tyr Gly Tyr Tyr
                160                 165                 170

Val Asn Pro Gly Pro Asn
    175

<210> SEQ ID NO 3
<211> LENGTH: 1257
<212> TYPE: DNA
<213> ORGANISM: Pseudomonas aeruginosa
<220> FEATURE:
<221> NAME/KEY: sig_peptide
<222> LOCATION: (1)..(93)
<220> FEATURE:
<221> NAME/KEY: CDS
<222> LOCATION: (94)..(1254)
<220> FEATURE:
<221> NAME/KEY: mat_peptide
<222> LOCATION: (709)..(1254)

<400> SEQUENCE: 3
atgcaacata aaagaagccg tgcgatggcg agcccgagaa gcccgttcct gtttgtgctg      60
ctggccctgg cggtgggtgg tactgccaac gcg cat gat gat ggc ctg ccg          111
                                    His Asp Asp Gly Leu Pro
                                    -205             -200 gca ttt cgt tat tca gcc gaa ctg ctg ggt caa ctg cag ctg ccg           156
Ala Phe Arg Tyr Ser Ala Glu Leu Leu Gly Gln Leu Gln Leu Pro
        -195                -190                 -185 tct gtg gca ctg ccg ctg aat gat gac ctg ttt ctg tat ggc cgt           201
Ser Val Ala Leu Pro Leu Asn Asp Asp Leu Phe Leu Tyr Gly Arg
        -180                -175                -170 gat gcg gaa gca ttt gat ctg gaa gcg tat ctg gca ctg aat gca           246
Asp Ala Glu Ala Phe Asp Leu Glu Ala Tyr Leu Ala Leu Asn Ala
        -165                -160                -155 ccg gca ctg cgt gat aaa agc gaa tat ctg gaa cat tgg tca ggc           291
Pro Ala Leu Arg Asp Lys Ser Glu Tyr Leu Glu His Trp Ser Gly
        -150                -145                -140 tat tat tct att aat ccg aaa gtt ctg ctg aca ctg atg gtc atg           336
Tyr Tyr Ser Ile Asn Pro Lys Val Leu Leu Thr Leu Met Val Met
        -135                -130                -125 caa agc ggt ccg ctg ggt gca ccg gat gaa cgt gca ctg gca gca           381
Gln Ser Gly Pro Leu Gly Ala Pro Asp Glu Arg Ala Leu Ala Ala
        -120                -115                -110
```

```
ccg ctg ggc cgt ctg tca gcc aaa cgc ggt ttt gat gcg cag gtg cgc    429
Pro Leu Gly Arg Leu Ser Ala Lys Arg Gly Phe Asp Ala Gln Val Arg
            -105            -100                    -95 gat gtt ctg cag cag ctg tct cgc cgt tat tat ggc ttt gaa gaa tat    477
Asp Val Leu Gln Gln Leu Ser Arg Arg Tyr Tyr Gly Phe Glu Glu Tyr
        -90              -85                  -80 caa ctg cgc cag gca gca gca cgt aaa gca gtt ggc gaa gat ggt ctg    525
Gln Leu Arg Gln Ala Ala Ala Arg Lys Ala Val Gly Glu Asp Gly Leu
        -75              -70              -65 aat gca gca tct gca gcg ctg ctg ggc ctg ctg cgt gaa ggt gca aaa    573
Asn Ala Ala Ser Ala Ala Leu Leu Gly Leu Leu Arg Glu Gly Ala Lys
    -60              -55              -50 gtc agc gca gtg cag ggc ggt aat ccg ctg ggt gca tat gcc cag acc    621
Val Ser Ala Val Gln Gly Gly Asn Pro Leu Gly Ala Tyr Ala Gln Thr
-45              -40              -35              -30 ttt cag cgc ctg ttt ggt aca ccg gcg gca gaa ctg ctg cag ccg tca    669
Phe Gln Arg Leu Phe Gly Thr Pro Ala Ala Glu Leu Leu Gln Pro Ser
            -25              -20              -15 aat cgt gtt gca cgt caa ctg cag gca aaa gcg gca ctg gca ccg ccg    717
Asn Arg Val Ala Arg Gln Leu Gln Ala Lys Ala Ala Leu Ala Pro Pro
        -10              -5               -1  1 agc aac ctg atg cag ctg ccg tgg cgt cag ggc tat tca tgg cag ccg    765
Ser Asn Leu Met Gln Leu Pro Trp Arg Gln Gly Tyr Ser Trp Gln Pro
    5                10                  15 aat ggt gca cat agc aac acg ggc tca ggt tat ccg tat agc tca ttt    813
Asn Gly Ala His Ser Asn Thr Gly Ser Gly Tyr Pro Tyr Ser Ser Phe
20              25                  30                  35 gat gcc agc tat gat tgg ccg cgt tgg ggc tct gca acc tat agc gtg    861
Asp Ala Ser Tyr Asp Trp Pro Arg Trp Gly Ser Ala Thr Tyr Ser Val
                40              45                  50 gtt gca gcc cat gcg ggt aca gtc cgc gtg ctg tct cgt tgc caa gtt    909
Val Ala Ala His Ala Gly Thr Val Arg Val Leu Ser Arg Cys Gln Val
            55              60                  65 cgt gtc aca cat ccg tct ggt tgg gca acc aat tat tat cat atg gat    957
Arg Val Thr His Pro Ser Gly Trp Ala Thr Asn Tyr Tyr His Met Asp
        70              75                  80 cag att cag gtg agc aac ggt cag cag gtt tca gca gat acg aaa ctg   1005
Gln Ile Gln Val Ser Asn Gly Gln Gln Val Ser Ala Asp Thr Lys Leu
    85              90              95 ggc gtt tat gca ggt aat atc aac aca gcc ctg tgc gaa ggc ggt tct   1053
Gly Val Tyr Ala Gly Asn Ile Asn Thr Ala Leu Cys Glu Gly Gly Ser
100             105             110                 115 agc acg ggc ccg cat ctg cat ttt tct ctg ctg tat aat ggt gcg ttt   1101
Ser Thr Gly Pro His Leu His Phe Ser Leu Leu Tyr Asn Gly Ala Phe
                120             125                 130 gtc tca ctg cag ggc gca tct ttt ggt ccg tat cgc atc aac gtg ggc   1149
Val Ser Leu Gln Gly Ala Ser Phe Gly Pro Tyr Arg Ile Asn Val Gly
            135             140             145 acc agc aat tat gat aac gat tgt cgc cgt tat tac ttc tac aat cag   1197
Thr Ser Asn Tyr Asp Asn Asp Cys Arg Arg Tyr Tyr Phe Tyr Asn Gln
        150             155             160 tct gct gga aca acc cac tgt gcc ttt aga ccg ctg tat aat ccg gga   1245
Ser Ala Gly Thr Thr His Cys Ala Phe Arg Pro Leu Tyr Asn Pro Gly
    165             170             175 ctg gct ctg taa                                                    1257
Leu Ala Leu
180

<210> SEQ ID NO 4
<211> LENGTH: 387
```

<212> TYPE: PRT
<213> ORGANISM: Pseudomonas aeruginosa

<400> SEQUENCE: 4

```
His Asp Asp Gly Leu Pro  Ala Phe Arg Tyr Ser  Ala Glu Leu Leu
-205              -200                 -195

Gly Gln Leu Gln Leu Pro  Ser Val Ala Leu Pro  Leu Asn Asp Asp
-190              -185                 -180

Leu Phe Leu Tyr Gly Arg  Asp Ala Glu Ala Phe  Asp Leu Glu Ala
-175              -170                 -165

Tyr Leu Ala Leu Asn Ala  Pro Ala Leu Arg Asp  Lys Ser Glu Tyr
-160              -155                 -150

Leu Glu His Trp Ser Gly  Tyr Tyr Ser Ile Asn  Pro Lys Val Leu
-145              -140                 -135

Leu Thr Leu Met Val Met  Gln Ser Gly Pro Leu  Gly Ala Pro Asp
-130              -125                 -120

Glu Arg Ala Leu Ala Ala  Pro Leu Gly Arg Leu  Ser Ala Lys Arg
-115              -110                 -105

Gly Phe Asp Ala Gln Val  Arg Asp Val Leu Gln  Gln Leu Ser Arg Arg
-100               -95                  -90                 -85

Tyr Tyr Gly Phe Glu Glu  Tyr Gln Leu Arg Gln  Ala Ala Arg Lys
                 -80                  -75                  -70

Ala Val Gly Glu Asp Gly  Leu Asn Ala Ala Ser  Ala Ala Leu Leu Gly
                 -65                  -60                  -55

Leu Leu Arg Glu Gly Ala  Lys Val Ser Ala Val  Gln Gly Gly Asn Pro
                 -50                  -45                  -40

Leu Gly Ala Tyr Ala Gln  Thr Phe Gln Arg Leu  Phe Gly Thr Pro Ala
                 -35                  -30                  -25

Ala Glu Leu Leu Gln Pro  Ser Asn Arg Val Ala  Arg Gln Leu Gln Ala
-20                -15                  -10                  -5

Lys Ala Ala Leu Ala Pro  Pro Ser Asn Leu Met  Gln Leu Pro Trp Arg
             -1  1                    5                    10

Gln Gly Tyr Ser Trp Gln  Pro Asn Gly Ala His  Ser Asn Thr Gly Ser
             15                    20                    25

Gly Tyr Pro Tyr Ser Ser  Phe Asp Ala Ser Tyr  Asp Trp Pro Arg Trp
             30                    35                    40

Gly Ser Ala Thr Tyr Ser  Val Val Ala Ala His  Ala Gly Thr Val Arg
45                   50                   55                   60

Val Leu Ser Arg Cys Gln  Val Arg Val Thr His  Pro Ser Gly Trp Ala
                 65                    70                    75

Thr Asn Tyr Tyr His Met  Asp Gln Ile Gln Val  Ser Asn Gly Gln Gln
                 80                    85                    90

Val Ser Ala Asp Thr Lys  Leu Gly Val Tyr Ala  Gly Asn Ile Asn Thr
                 95                   100                   105

Ala Leu Cys Glu Gly Gly  Ser Ser Thr Gly Pro  His Leu His Phe Ser
                110                   115                   120

Leu Leu Tyr Asn Gly Ala  Phe Val Ser Leu Gln  Gly Ala Ser Phe Gly
125                  130                   135                  140

Pro Tyr Arg Ile Asn Val  Gly Thr Ser Asn Tyr  Asp Asn Asp Cys Arg
                145                   150                   155

Arg Tyr Tyr Phe Tyr Asn  Gln Ser Ala Gly Thr  Thr His Cys Ala Phe
                160                   165                   170

Arg Pro Leu Tyr Asn Pro  Gly Leu Ala Leu
                175                   180
```

<210> SEQ ID NO 5
<211> LENGTH: 1164
<212> TYPE: DNA
<213> ORGANISM: Aeromonas hydrophila
<220> FEATURE:
<221> NAME/KEY: sig_peptide
<222> LOCATION: (1)..(60)
<220> FEATURE:
<221> NAME/KEY: CDS
<222> LOCATION: (61)..(1161)
<220> FEATURE:
<221> NAME/KEY: mat_peptide
<222> LOCATION: (625)..(1161)

<400> SEQUENCE: 5

```
atgtctcgtc cgatcccgtc cctgctgatg ctggctctgc tgccggctgc tggttgggct      60 ggc gat att cac gct ccg ctg gct ccg tat cat ttt acg gcg cag           105
Gly Asp Ile His Ala Pro Leu Ala Pro Tyr His Phe Thr Ala Gln
        -185            -180                -175 caa ctg gca gca tct caa acc ccg gca ctg ccg ctg gat gaa gca           150
Gln Leu Ala Ala Ser Gln Thr Pro Ala Leu Pro Leu Asp Glu Ala
    -170                -165                -160 cat ttt gtt ttt ggc gaa gcc gcg atg gca ttt gat ctg cat gat           195
His Phe Val Phe Gly Glu Ala Ala Met Ala Phe Asp Leu His Asp
        -155                -150                -145 ttt ctg ctg cag cag gcc ccg cat ctg ctg ccg aaa gaa gaa gtc           240
Phe Leu Leu Gln Gln Ala Pro His Leu Leu Pro Lys Glu Glu Val
    -140                -135                -130 att ctg cat tgg agc ggt atc acg tca ctg aat ccg cag ctg ctg           285
Ile Leu His Trp Ser Gly Ile Thr Ser Leu Asn Pro Gln Leu Leu
        -125                -120                -115 ctg gcc ctg atg gaa gcg agc tca cag ctg att tca gca ccg tct           330
Leu Ala Leu Met Glu Ala Ser Ser Gln Leu Ile Ser Ala Pro Ser
    -110                -105                -100 gaa cag gcc atg gca gcc ccg ttt gcg aaa ctg gtg aat gca cgt ggc       378
Glu Gln Ala Met Ala Ala Pro Phe Ala Lys Leu Val Asn Ala Arg Gly
        -95                 -90                 -85 ttt gat aac cag ctg gaa ctg atg gcc cgc cag ctg tct gaa cgt ttt       426
Phe Asp Asn Gln Leu Glu Leu Met Ala Arg Gln Leu Ser Glu Arg Phe
    -80                  -75                 -70 tat cag gca cgc gcc cag cag aaa ctg atg caa cgt tct gca ccg gca       474
Tyr Gln Ala Arg Ala Gln Gln Lys Leu Met Gln Arg Ser Ala Pro Ala
        -65                 -60                 -55 ctg gcc ccg cag gcg gca cat cag gcc gcg ctg gca tca atg ctg tct       522
Leu Ala Pro Gln Ala Ala His Gln Ala Ala Leu Ala Ser Met Leu Ser
-50                  -45                 -40                 -35 acc agc atg cag cgt cag ctg ggc gaa cag tgg cag acc ctg ttt ggt       570
Thr Ser Met Gln Arg Gln Leu Gly Glu Gln Trp Gln Thr Leu Phe Gly
            -30                 -25                 -20 caa gat gca atg aca agc ccg cgc ggc ggt gca gca gca ccg gca gcc       618
Gln Asp Ala Met Thr Ser Pro Arg Gly Gly Ala Ala Ala Pro Ala Ala
        -15                 -10                 -5 ccg ctg gca ggc ggt caa ttt cag ctg ccg tgg cgt cag ggc tat tct       666
Pro Leu Ala Gly Gly Gln Phe Gln Leu Pro Trp Arg Gln Gly Tyr Ser
-1  1                    5                  10 tgg aaa gcg aat ggt gca cat tct cat aca ggc agc ggt tat ccg tat       714
Trp Lys Ala Asn Gly Ala His Ser His Thr Gly Ser Gly Tyr Pro Tyr
15                   20                  25                  30 tct agc atc gat gtc agc tat gat tgg ccg ggt tgg ggc ggt gcg acc       762
Ser Ser Ile Asp Val Ser Tyr Asp Trp Pro Gly Trp Gly Gly Ala Thr
                    35                  40                  45
```

```
tat aca gtg acg gcg gca aac tca ggt acc gtg aca gtg ttt agc cgt     810
Tyr Thr Val Thr Ala Ala Asn Ser Gly Thr Val Thr Val Phe Ser Arg
            50                  55                  60 tgc cag gtc cgt gtg aca gca acc aat ggc tgg gca aca aac tat tat     858
Cys Gln Val Arg Val Thr Ala Thr Asn Gly Trp Ala Thr Asn Tyr Tyr
        65                  70                  75 cat atg agc ggc att tca gtg cgt tct ggt gat tat gtt gcc gcg gat     906
His Met Ser Gly Ile Ser Val Arg Ser Gly Asp Tyr Val Ala Ala Asp
    80                  85                  90 aca ccg atc ggc acg tat gcc tca aat cgc aac gaa gcg ctg tgc gaa     954
Thr Pro Ile Gly Thr Tyr Ala Ser Asn Arg Asn Glu Ala Leu Cys Glu
95                  100                 105                 110 ggc ggt tca tct acg ggt ccg cat ctg cat ttt agc ctg ctg tat aat    1002
Gly Gly Ser Ser Thr Gly Pro His Leu His Phe Ser Leu Leu Tyr Asn
                115                 120                 125 ggc gtt ttt cag tca ctg cag ggt cag cgt ctg agc tca tat gca gtt    1050
Gly Val Phe Gln Ser Leu Gln Gly Gln Arg Leu Ser Ser Tyr Ala Val
            130                 135                 140 aat gtc ggc gcc agc aac tat gat gat aat tgt aac cgc ttt tgg ctg    1098
Asn Val Gly Ala Ser Asn Tyr Asp Asp Asn Cys Asn Arg Phe Trp Leu
        145                 150                 155 tat aac caa aga aac gga caa cgc tac tgt gct tgg caa ccg ctg tat    1146
Tyr Asn Gln Arg Asn Gly Gln Arg Tyr Cys Ala Trp Gln Pro Leu Tyr
    160                 165                 170 aat aac gga atc gac taa                                             1164
Asn Asn Gly Ile Asp
175

<210> SEQ ID NO 6
<211> LENGTH: 367
<212> TYPE: PRT
<213> ORGANISM: Aeromonas hydrophila

<400> SEQUENCE: 6

Gly Asp Ile His  Ala Pro Leu Ala  Pro Tyr His Phe  Thr Ala  Gln
            -185              -180               -175

Gln Leu Ala Ala  Ser Gln Thr Pro  Ala Leu Pro Leu  Asp Glu  Ala
        -170              -165               -160

His Phe Val Phe  Gly Glu Ala Ala  Met Ala Phe Asp  Leu His  Asp
        -155              -150               -145

Phe Leu Leu Gln  Gln Ala Pro His  Leu Leu Pro Lys  Glu Glu  Val
        -140              -135               -130

Ile Leu His Trp  Ser Gly Ile Thr  Ser Leu Asn Pro  Gln Leu  Leu
        -125              -120               -115

Leu Ala Leu Met  Glu Ala Ser Ser  Gln Leu Ile Ser  Ala Pro  Ser
        -110              -105               -100

Glu Gln Ala Met  Ala Ala Pro Phe  Ala Lys Leu Val  Asn Ala Arg Gly
        -95               -90                -85

Phe Asp Asn Gln  Leu Glu Leu Met  Ala Arg Gln Leu  Ser Glu Arg Phe
        -80               -75                -70

Tyr Gln Ala Arg  Ala Gln Gln Lys  Leu Met Gln Arg  Ser Ala Pro Ala
        -65               -60                -55

Leu Ala Pro Gln  Ala Ala His Gln  Ala Ala Leu Ala  Ser Met Leu Ser
-50                -45                -40                -35

Thr Ser Met Gln  Arg Gln Leu Gly  Glu Gln Trp Gln  Thr Leu Phe Gly
            -30                -25                -20

Gln Asp Ala Met  Thr Ser Pro Arg  Gly Gly Ala Ala  Ala Pro Ala Ala
```

```
                -15                 -10                 -5
Pro Leu Ala Gly Gly Gln Phe Gln Leu Pro Trp Arg Gln Gly Tyr Ser
    -1  1                   5                  10
Trp Lys Ala Asn Gly Ala His Ser His Thr Gly Ser Gly Tyr Pro Tyr
15                  20                  25                  30
Ser Ser Ile Asp Val Ser Tyr Asp Trp Pro Gly Trp Gly Ala Thr
                35                  40                  45
Tyr Thr Val Thr Ala Ala Asn Ser Gly Thr Val Thr Val Phe Ser Arg
                50                  55                  60
Cys Gln Val Arg Val Thr Ala Thr Asn Gly Trp Ala Thr Asn Tyr Tyr
                65                  70                  75
His Met Ser Gly Ile Ser Val Arg Ser Gly Asp Tyr Val Ala Ala Asp
80                  85                  90
Thr Pro Ile Gly Thr Tyr Ala Ser Asn Arg Asn Glu Ala Leu Cys Glu
95                 100                 105                 110
Gly Gly Ser Ser Thr Gly Pro His Leu His Phe Ser Leu Leu Tyr Asn
                115                 120                 125
Gly Val Phe Gln Ser Leu Gln Gly Gln Arg Leu Ser Ser Tyr Ala Val
                130                 135                 140
Asn Val Gly Ala Ser Asn Tyr Asp Asp Asn Cys Asn Arg Phe Trp Leu
                145                 150                 155
Tyr Asn Gln Arg Asn Gly Gln Arg Tyr Cys Ala Trp Gln Pro Leu Tyr
160                 165                 170
Asn Asn Gly Ile Asp
175

<210> SEQ ID NO 7
<211> LENGTH: 1164
<212> TYPE: DNA
<213> ORGANISM: Lysobacter gummosus
<220> FEATURE:
<221> NAME/KEY: sig_peptide
<222> LOCATION: (1)..(99)
<220> FEATURE:
<221> NAME/KEY: CDS
<222> LOCATION: (100)..(1161)
<220> FEATURE:
<221> NAME/KEY: mat_peptide
<222> LOCATION: (628)..(1161)

<400> SEQUENCE: 7
atgtctaaca aaacaggatc taaccaggca ttttctaaaa tgggattagc attattaaca      60
tgctgcgttt tagcagcaat ctctggagga gcaggagca gcg gaa cgt ggt ctg       114
                                             Ala Glu Arg Gly Leu
                                                     -175 agc ggc cag gac ctg gtt tat agc tac gat gaa atg ttt gat ttc          159
Ser Gly Gln Asp Leu Val Tyr Ser Tyr Asp Glu Met Phe Asp Phe
    -170                -165                 -160 gac att gat gcg tac ctg gcg aaa aac gcg ccg cat ctg agc cgt          204
Asp Ile Asp Ala Tyr Leu Ala Lys Asn Ala Pro His Leu Ser Arg
    -155                -150                 -145 cac gcg gaa agc atc agc cat tgg gcg ggt tat agc ggc att agc          249
His Ala Glu Ser Ile Ser His Trp Ala Gly Tyr Ser Gly Ile Ser
    -140                -135                 -130 ccg aaa gtg ctg atc gcg ctg atg gaa cag caa agc ggc gcg att          294
Pro Lys Val Leu Ile Ala Leu Met Glu Gln Gln Ser Gly Ala Ile
    -125                -120                 -115 acc cgt aaa cat gca gca gca gat gca gca aaa cgt ccg ttt ggt          339
Thr Arg Lys His Ala Ala Ala Asp Ala Ala Lys Arg Pro Phe Gly
```

```
                -110                -105              -100
gca ctg gcg aaa gcg aaa gat ttc aat ggt cag acc cgt gaa gtt gcg         387
Ala Leu Ala Lys Ala Lys Asp Phe Asn Gly Gln Thr Arg Glu Val Ala
    -95             -90                 -85 caa gcg ctg cgt gaa gcg ctg tac gaa aac gac ggt ccg gat gca aag         435
Gln Ala Leu Arg Glu Ala Leu Tyr Glu Asn Asp Gly Pro Asp Ala Lys
-80             -75                 -70                 -65 ggt gca gtt acc gtg gca cgt gca aat ccg ctg cag gca ctg ttt gaa         483
Gly Ala Val Thr Val Ala Arg Ala Asn Pro Leu Gln Ala Leu Phe Glu
                -60                 -55                 -50 cgt gcg ggt gca agc caa gca agc gca aaa ctg agc ggt gac ggc gaa         531
Arg Ala Gly Ala Ser Gln Ala Ser Ala Lys Leu Ser Gly Asp Gly Glu
                -45                 -40                 -35 ttt cag ctg gtg tat ggt cgt ctg ttc aac gaa ccg cgt cag gca cag         579
Phe Gln Leu Val Tyr Gly Arg Leu Phe Asn Glu Pro Arg Gln Ala Gln
        -30                 -25                 -20 gca ccg agc gca cgt ttt gca aaa gcg ggt ccg gat gtt cag ccg ctg         627
Ala Pro Ser Ala Arg Phe Ala Lys Ala Gly Pro Asp Val Gln Pro Leu
        -15                 -10                 -5              -1 agc ccg aat ggc ctg ctg caa ttt ccg ttt ccg cgt ggt gcg cgt tgg         675
Ser Pro Asn Gly Leu Leu Gln Phe Pro Phe Pro Arg Gly Ala Arg Trp
1                5                   10                  15 cat gtg ggc ggt gcg cac acc aac acc ggt agc ggc aat tac ccg atg         723
His Val Gly Gly Ala His Thr Asn Thr Gly Ser Gly Asn Tyr Pro Met
                20                  25                  30 agc agc ctg gac atg agc ctg ggc ggt ggc tgg ggc agc aac caa agc         771
Ser Ser Leu Asp Met Ser Leu Gly Gly Gly Trp Gly Ser Asn Gln Ser
            35                  40                  45 aat acc tgg gtt agc gcg agc gcg aac ggt agc ttt aaa cgt cat agc         819
Asn Thr Trp Val Ser Ala Ser Ala Asn Gly Ser Phe Lys Arg His Ser
50                  55                  60 agc tgc ttc gcg gaa att gtg cac agc ggt ggc tgg agc acc acc tat         867
Ser Cys Phe Ala Glu Ile Val His Ser Gly Gly Trp Ser Thr Thr Tyr
65              70                  75                  80 tac cat ctg atg aac att cgt tac aat acc ggt gcg aac gtt ggc agc         915
Tyr His Leu Met Asn Ile Arg Tyr Asn Thr Gly Ala Asn Val Gly Ser
                85                  90                  95 aat acc gcg att gca aat ccg gca aat acc cgt gca cag gca ctg tgc         963
Asn Thr Ala Ile Ala Asn Pro Ala Asn Thr Arg Ala Gln Ala Leu Cys
                100                 105                 110 aat ggt ggc agc agc acc ggc ccg cat gaa cac tgg agc ctg aaa ctg        1011
Asn Gly Gly Ser Ser Thr Gly Pro His Glu His Trp Ser Leu Lys Leu
            115                 120                 125 aac ggt agc ttt tat cat ctg aat ggt gcg tat ctg agc ggc tac cgt        1059
Asn Gly Ser Phe Tyr His Leu Asn Gly Ala Tyr Leu Ser Gly Tyr Arg
        130                 135                 140 atc acc gcg acc ggc agc agc tat gat acc aac tgc agc cgt ttt tac        1107
Ile Thr Ala Thr Gly Ser Ser Tyr Asp Thr Asn Cys Ser Arg Phe Tyr
145                 150                 155                 160 ctg gcg aaa aac ggt caa aat tat tgc agc ggc tgg ttc acc aat ccg        1155
Leu Ala Lys Asn Gly Gln Asn Tyr Cys Ser Gly Trp Phe Thr Asn Pro
                165                 170                 175 ggt cac taa                                                             1164
Gly His <210> SEQ ID NO 8
<211> LENGTH: 354
<212> TYPE: PRT
<213> ORGANISM: Lysobacter gummosus
```

<400> SEQUENCE: 8

```
Ala Glu Arg Gly Leu Ser Gly Gln Asp Leu Val Tyr Ser Tyr Asp
    -175                -170                -165

Glu Met Phe Asp Phe Asp Ile Asp Ala Tyr Leu Ala Lys Asn Ala
    -160                -155                -150

Pro His Leu Ser Arg His Ala Glu Ser Ile Ser His Trp Ala Gly
    -145                -140                -135

Tyr Ser Gly Ile Ser Pro Lys Val Leu Ile Ala Leu Met Glu Gln
    -130                -125                -120

Gln Ser Gly Ala Ile Thr Arg Lys His Ala Ala Ala Asp Ala Ala
    -115                -110                -105

Lys Arg Pro Phe Gly Ala Leu Ala Lys Ala Lys Asp Phe Asn Gly Gln
    -100                 -95                 -90

Thr Arg Glu Val Ala Gln Ala Leu Arg Glu Ala Leu Tyr Glu Asn Asp
-85                  -80                  -75                  -70

Gly Pro Asp Ala Lys Gly Ala Val Thr Val Ala Arg Ala Asn Pro Leu
                     -65                  -60                  -55

Gln Ala Leu Phe Glu Arg Ala Gly Ala Ser Gln Ala Ser Ala Lys Leu
                     -50                  -45                  -40

Ser Gly Asp Gly Glu Phe Gln Leu Val Tyr Gly Arg Leu Phe Asn Glu
                     -35                  -30                  -25

Pro Arg Gln Ala Gln Ala Pro Ser Ala Arg Phe Ala Lys Ala Gly Pro
                     -20                  -15                  -10

Asp Val Gln Pro Leu Ser Pro Asn Gly Leu Leu Gln Phe Pro Phe Pro
-5                    -1   1                    5                     10

Arg Gly Ala Arg Trp His Val Gly Gly Ala His Thr Asn Thr Gly Ser
                          15                   20                   25

Gly Asn Tyr Pro Met Ser Ser Leu Asp Met Ser Leu Gly Gly Trp
                30                   35                   40

Gly Ser Asn Gln Ser Asn Thr Trp Val Ser Ala Ser Ala Asn Gly Ser
                45                   50                   55

Phe Lys Arg His Ser Ser Cys Phe Ala Glu Ile Val His Ser Gly Gly
60                   65                   70                   75

Trp Ser Thr Thr Tyr Tyr His Leu Met Asn Ile Arg Tyr Asn Thr Gly
                80                   85                   90

Ala Asn Val Gly Ser Asn Thr Ala Ile Ala Asn Pro Ala Asn Thr Arg
                95                  100                  105

Ala Gln Ala Leu Cys Asn Gly Gly Ser Ser Thr Gly Pro His Glu His
                110                  115                  120

Trp Ser Leu Lys Leu Asn Gly Ser Phe Tyr His Leu Asn Gly Ala Tyr
                125                  130                  135

Leu Ser Gly Tyr Arg Ile Thr Ala Thr Gly Ser Ser Tyr Asp Thr Asn
140                  145                  150                  155

Cys Ser Arg Phe Tyr Leu Ala Lys Asn Gly Gln Asn Tyr Cys Ser Gly
                160                  165                  170

Trp Phe Thr Asn Pro Gly His
                175
```

<210> SEQ ID NO 9
<211> LENGTH: 1164
<212> TYPE: DNA
<213> ORGANISM: Lysobacter antibioticus
<220> FEATURE:
<221> NAME/KEY: sig_peptide
<222> LOCATION: (1)..(77)

<220> FEATURE:
<221> NAME/KEY: CDS
<222> LOCATION: (79)..(1161)
<220> FEATURE:
<221> NAME/KEY: mat_peptide
<222> LOCATION: (628)..(1161)

<400> SEQUENCE: 9

```
atgaaagcaa tctctaaagc aagattagga ttattagcat gctgcatcgc agcagcaatc      60
ggaggaacag caacagca ggc ggt cgt gat gcg aat gca gca gca ggt ctg       111
                   Gly Gly Arg Asp Ala Asn Ala Ala Ala Gly Leu
                                -180                -175 agc ggt cag gat ctg gtt tat agc tac gac gaa atg ttt gat ttc           156
Ser Gly Gln Asp Leu Val Tyr Ser Tyr Asp Glu Met Phe Asp Phe
        -170                -165                -160 gac acc gcg gcg tat ctg gcg aaa cat gcg ccg cac ctg gtt cgt           201
Asp Thr Ala Ala Tyr Leu Ala Lys His Ala Pro His Leu Val Arg
        -155                -150                -145 cat agc gaa agc att agc cac tgg gcg ggt tac agc agc att agc           246
His Ser Glu Ser Ile Ser His Trp Ala Gly Tyr Ser Ser Ile Ser
        -140                -135                -130 ccg aaa gtg ctg atc gcg ctg atg gaa cag caa agc ggt gtt gtg           291
Pro Lys Val Leu Ile Ala Leu Met Glu Gln Gln Ser Gly Val Val
        -125                -120                -115 agc cgt caa cgt gca agc gca gat gca atg cgt cgt ccg ttt ggc           336
Ser Arg Gln Arg Ala Ser Ala Asp Ala Met Arg Arg Pro Phe Gly
        -110                -105                -100 aaa ctg agc gcg gcg aaa gac ttc aat agc cag acc cgt gaa gtt gcg       384
Lys Leu Ser Ala Ala Lys Asp Phe Asn Ser Gln Thr Arg Glu Val Ala
        -95                 -90                 -85 acc gcg ctg cgt cag gcg ctg tat gaa caa gaa gat gcg agc ctg gcg       432
Thr Ala Leu Arg Gln Ala Leu Tyr Glu Gln Glu Asp Ala Ser Leu Ala
        -80                 -75                 -70 ccg caa ggt cgt gtt ccg ctg gca cgt agc aac ccg ctg cag gcg ctg       480
Pro Gln Gly Arg Val Pro Leu Ala Arg Ser Asn Pro Leu Gln Ala Leu
-65                 -60                 -55                 -50 tat ctg caa gca ggt gaa agc cag gca agc gca gca ctg cgt ggt gac       528
Tyr Leu Gln Ala Gly Glu Ser Gln Ala Ser Ala Ala Leu Arg Gly Asp
            -45                 -40                 -35 ggc gaa ttt cag caa gtg tac ggt cgt ctg ttc aat gaa ccg cgt aag       576
Gly Glu Phe Gln Gln Val Tyr Gly Arg Leu Phe Asn Glu Pro Arg Lys
            -30                 -25                 -20 gca gca ccg gca agc gca cgt ttt gca gat acc agc gat gtt aat gca       624
Ala Ala Pro Ala Ser Ala Arg Phe Ala Asp Thr Ser Asp Val Asn Ala
            -15                 -10                 -5 ctg gca ggt ccg gcg aat ggc ttt ctg cag ttc ccg tat ccg cgt ggc       672
Leu Ala Gly Pro Ala Asn Gly Phe Leu Gln Phe Pro Tyr Pro Arg Gly
-1  1               5                   10                  15 gcg agc tgg cat gtg ggc ggt gcg cac acc aac acc ggt agc ggc aat       720
Ala Ser Trp His Val Gly Gly Ala His Thr Asn Thr Gly Ser Gly Asn
                20                  25                  30 tac ccg atg agc agc ctg gat atg agc cgt ggc ggt ggc tgg ggt agc       768
Tyr Pro Met Ser Ser Leu Asp Met Ser Arg Gly Gly Gly Trp Gly Ser
            35                  40                  45 aac caa agc ggc aat tgg gtt agc gcg agc gcg ggt ggc agc ttt aaa       816
Asn Gln Ser Gly Asn Trp Val Ser Ala Ser Ala Gly Gly Ser Phe Lys
            50                  55                  60 cgt cat agc agc tgc ttc gcg gaa gtt gtg cac agc ggt ggc tgg agc       864
Arg His Ser Ser Cys Phe Ala Glu Val Val His Ser Gly Gly Trp Ser
65                  70                  75
```

```
acc acc tat tac cat atg atg aac ctg caa tat ggt acc ggt gcg agc       912
Thr Thr Tyr Tyr His Met Met Asn Leu Gln Tyr Gly Thr Gly Ala Ser
80              85                  90                  95 gtg gca gca aat agc cgt att ggt aat ccg gca aat acc cgt gca cag       960
Val Ala Ala Asn Ser Arg Ile Gly Asn Pro Ala Asn Thr Arg Ala Gln
            100                 105                 110 gca ctg tgc aat ggt ggc gcg agc acc ggt ccg cat gaa cac tgg agc      1008
Ala Leu Cys Asn Gly Gly Ala Ser Thr Gly Pro His Glu His Trp Ser
                115                 120                 125 ctg aaa tat aac ggc agc cat tac cac ctg aat ggt gtt tat ctg agc      1056
Leu Lys Tyr Asn Gly Ser His Tyr His Leu Asn Gly Val Tyr Leu Ser
        130                 135                 140 ggc tac caa atc acc gcg ctg ggc agc agc tat gac acc aac tgc agc      1104
Gly Tyr Gln Ile Thr Ala Leu Gly Ser Ser Tyr Asp Thr Asn Cys Ser
    145                 150                 155 cgt ttt tac ctg agc aaa aat ggt agc cgt tat tgc agc ggc tac ttc      1152
Arg Phe Tyr Leu Ser Lys Asn Gly Ser Arg Tyr Cys Ser Gly Tyr Phe
160                 165                 170                 175 acc aat ccg taa                                                       1164
Thr Asn Pro <210> SEQ ID NO 10
<211> LENGTH: 361
<212> TYPE: PRT
<213> ORGANISM: Lysobacter antibioticus

<400> SEQUENCE: 10

Gly Gly Arg Asp  Ala Asn Ala Ala  Ala Gly Leu Ser Gly Gln  Asp
                -180             -175                    -170

Leu Val Tyr Ser  Tyr Asp Glu Met  Phe Asp Phe Asp Thr Ala  Ala
                -165             -160                    -155

Tyr Leu Ala Lys  His Ala Pro His  Leu Val Arg His Ser Glu  Ser
                -150             -145                    -140

Ile Ser His Trp  Ala Gly Tyr Ser  Ser Ile Ser Pro Lys Val  Leu
                -135             -130                    -125

Ile Ala Leu Met  Glu Gln Gln Ser  Gly Val Val Ser Arg Gln  Arg
                -120             -115                    -110

Ala Ser Ala Asp  Ala Met Arg Arg  Pro Phe Gly Lys Leu Ser Ala Ala
                -105             -100                    -95

Lys Asp Phe Asn Ser Gln Thr Arg Glu Val Ala Thr Ala Leu Arg Gln
    -90                 -85                  -80

Ala Leu Tyr Glu Gln Glu Asp Ala Ser Leu Ala Pro Gln Gly Arg Val
    -75                 -70                  -65

Pro Leu Ala Arg Ser Asn Pro Leu Gln Ala Leu Tyr Leu Gln Ala Gly
-60                 -55                  -50                 -45

Glu Ser Gln Ala Ser Ala Ala Leu Arg Gly Asp Gly Glu Phe Gln Gln
                -40                 -35                 -30

Val Tyr Gly Arg Leu Phe Asn Glu Pro Arg Lys Ala Ala Pro Ala Ser
            -25                 -20                  -15

Ala Arg Phe Ala Asp Thr Ser Asp Val Asn Ala Leu Ala Gly Pro Ala
        -10                 -5                   -1  1

Asn Gly Phe Leu Gln Phe Pro Tyr Pro Arg Gly Ala Ser Trp His Val
5                   10                  15                  20

Gly Gly Ala His Thr Asn Thr Gly Ser Gly Asn Tyr Pro Met Ser Ser
                25                  30                  35

Leu Asp Met Ser Arg Gly Gly Gly Trp Gly Ser Asn Gln Ser Gly Asn
        40                  45                  50
```

```
Trp Val Ser Ala Ser Ala Gly Gly Ser Phe Lys Arg His Ser Ser Cys
    55                  60                  65
Phe Ala Glu Val Val His Ser Gly Gly Trp Ser Thr Thr Tyr Tyr His
    70                  75                  80
Met Met Asn Leu Gln Tyr Gly Thr Gly Ala Ser Val Ala Ala Asn Ser
85                  90                  95                  100
Arg Ile Gly Asn Pro Ala Asn Thr Arg Ala Gln Ala Leu Cys Asn Gly
                105                 110                 115
Gly Ala Ser Thr Gly Pro His Glu His Trp Ser Leu Lys Tyr Asn Gly
                120                 125                 130
Ser His Tyr His Leu Asn Gly Val Tyr Leu Ser Gly Tyr Gln Ile Thr
            135                 140                 145
Ala Leu Gly Ser Ser Tyr Asp Thr Asn Cys Ser Arg Phe Tyr Leu Ser
        150                 155                 160
Lys Asn Gly Ser Arg Tyr Cys Ser Gly Tyr Phe Thr Asn Pro
165                 170                 175
```

LEATHER IMPROVING AGENT

FIELD OF THE INVENTION

The present invention relates to a leather improving agent which is used for production of natural leather.

BACKGROUND OF THE INVENTION

Animal natural leather is widely used in daily life for, for example, footwears such as shoes, clothes and accessories such as bags, handbags, clothing, gloves and belts, furniture such as chairs, interiors and car seats, sporting goods, horse harnesses, drums and handicrafts, and is an important material for household items.

Production of natural leather can be divided into four major steps, i.e. 1) a preparatory operation, 2) a tanning step, 3) a retanning/dyeing/fatliquoring step and 4) a finishing step. In the preparatory operation, blood, dirt, salts, pieces of meat, fat and the like deposited on raw hide are removed, the hide is swollen with lime and a sulfide to loosen collagen fibers and also to degrade and remove hair, and undesired protein is degraded and removed by bating, so that the grain side is smoothed.

The bating, which is also referred to as enzymatic degradation, is an enzyme treatment step which is applied to limed and delimed hide for the purpose of, for example, i) removing hair roots, protein degradation products, fat and the like remaining on the hide, ii) removing substances between fibers of the hide, iii) removing elastin fibers causing the hide to contract, and the like, iv) smoothing the grain side of the hide, and v) mildly unraveling collagen fibers.

Therefore, an enzyme used for bating is required to exhibit the above-described effects. For example, it is known that by degrading elastin in leather by an enzyme having an ability to degrade elastin, contraction of the leather can be suppressed to enlarge the area (Patent Literature 1), but simultaneously, there arises a problem that degradation of collagen, which is a main component of the hide, results in a decrease in strength. As a technique for suppressing contraction of hide to enlarge the area while suppressing collagen degradation, a method has been heretofore proposed in which hide is treated with a mixture of a protease and elastase after chrome tanning (Non Patent Literature 2). In such a method, however, the type of tanning step is limited, and it is necessary to change the production process itself.

On the other hand, the M23 family of proteases is a protease family defined in the MEROPS database as proteases capable of degrading a Gly-Gly bond, has degrading activity on elastin and proteoglycan of bacterial cell walls, and is also known as a bacteriolytic enzyme. Among them, β-lytic protease (BLP) belonging to the M23A subfamily has been reported to have strong bacteriolytic activity on gram-positive bacteria such as *Bacillus subtilis* (Patent Literature 3). It has been recently found that an M23A subfamily protease can be efficiently produced from a culture by introducing an M23A family protease gene into a *Bacillus* bacterial host and culturing the bacteria (Patent Literature 4).

However, utilization of an M23A family protease as an enzyme for production of leather has not been heretofore reported.

[Patent Literature 1] WO 2001/035901
[Patent Literature 2] WO 2002/088397
[Patent Literature 3] JP-A-4-108387
[Patent Literature 4] WO 2019/142773

SUMMARY OF INVENTION

The present invention relates to the following 1) to 4).
1) A method for treating leather, comprising a step of bringing an M23A subfamily protease or an enzyme composition comprising the M23A subfamily protease into contact with a hide.
2) A leather improving agent comprising an M23A subfamily protease as an active ingredient.
3) Use of an M23A subfamily protease for producing a leather improving agent.
4) Use of an M23A subfamily protease for improving leather.

DESCRIPTION OF EMBODIMENTS

Figure 1:
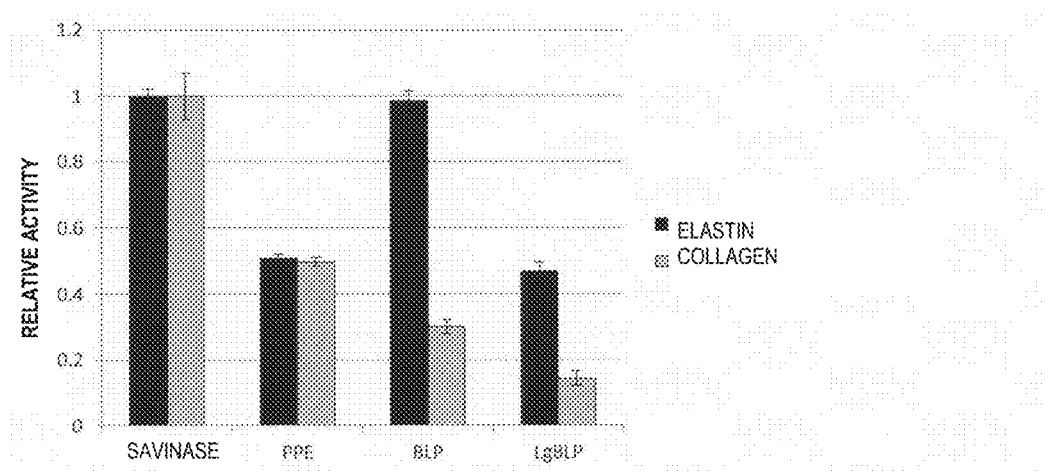
FIG. 1 shows degrading activity of BLP on elastin and collagen (relative value to savinase).
Figure 2:
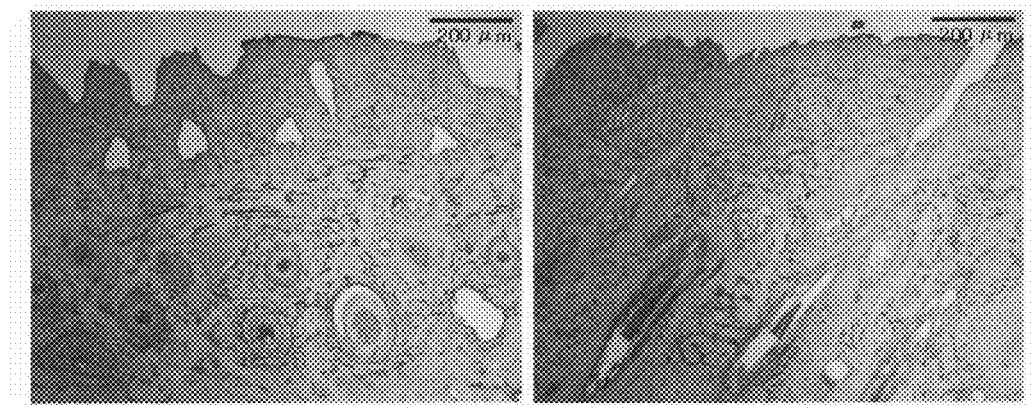
FIG. 2 shows a degrading effect on elastin of bovine hide (without enzyme treatment).
Figure 3:
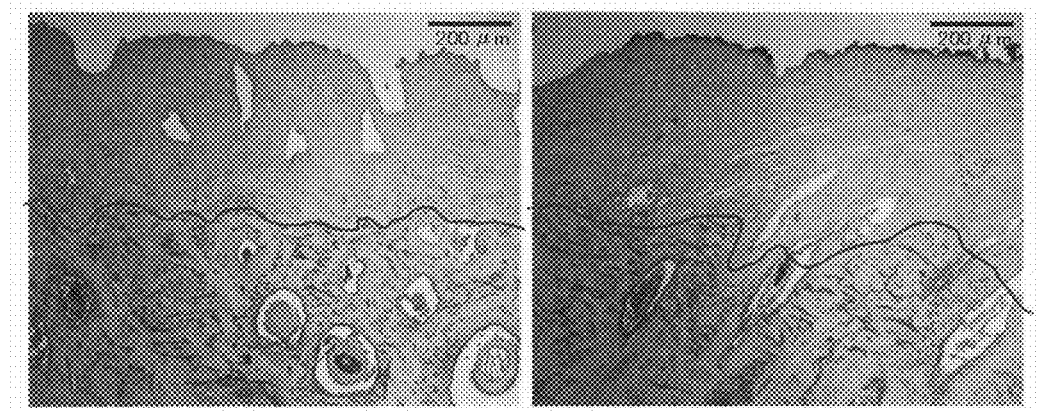
FIG. 3 shows a degrading effect on elastin of bovine hide (savinase treatment). The dark, solid line that bisects the figure from left to right indicates a boundary between an elastin-degraded part and an elastin-remaining part.
Figure 4:
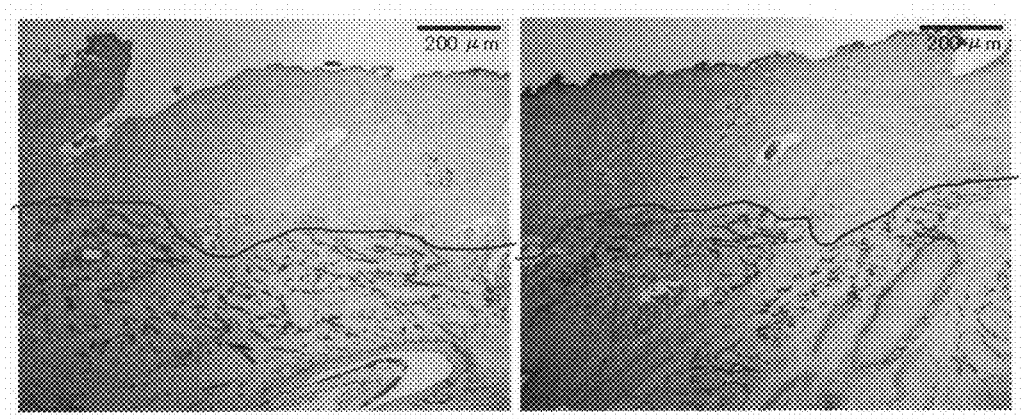
FIG. 4 shows a degrading effect on elastin of bovine hide (PPE treatment). The dark, solid line that bisects the figure from left to right indicates a boundary between an elastin-degraded part and an elastin-remaining part.
Figure 5:
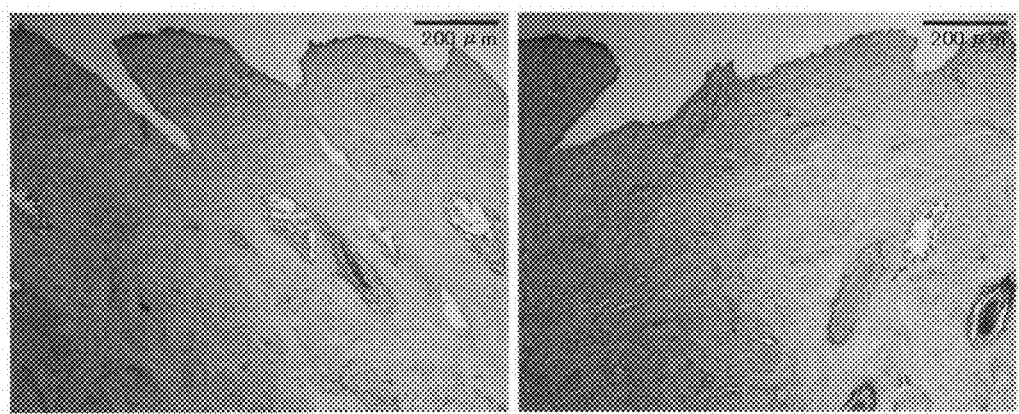
FIG. 5 shows a degrading effect on elastin of bovine hide (BLP treatment).

The present invention relates to a provision of a leather improving agent which exhibits the effect of suppressing contraction of hide to enlarge the area, and a method for treating leather using the leather improving agent.

The present inventor found that an M23A subfamily protease typified by BLP can efficiently degrade elastin at a deep part of hide with little degradation of collagen, and is useful as an enzyme which exhibits the effect of suppressing contraction of hide.

The enzyme provided by the present invention, i.e. an M23A subfamily protease, has little collagen degrading activity, and has an excellent ability to efficiently degrade elastin at a deep part of hide. By using such an enzyme in a leather treatment process, contraction of hide can be suppressed to enlarge the area.

As used herein, the "hide" means hide of an animal such as bovine, a pig, a deer, sheep, a horse, a goat, a kangaroo or a crocodile.

As used herein, the "identity of at least 80%" for nucleotide sequences or amino acid sequences is an identity of 80% or more, preferably 85% or more, more preferably 90% or more, even more preferably 95, or more, even more preferably 97% or more, even preferably 98% or more, even more preferably 99% or more.

As used herein, the identity between nucleotide sequences or amino acid sequences can be calculated by the Lipman-Pearson method (Science, 1985, 227: 1435-41). Specifically, the identity can be calculated by performing analysis by using the homology analysis (search homology) program of genetic information processing software Genetryx-Win (ver. 5.1.1; software development) and setting the unit size to compare (ktup) to 2.

As used herein, the "position corresponding to . . . " on amino acid sequences and nucleotide sequences can be determined by aligning a target sequence and a reference sequence (e.g. an amino acid sequence set forth as SEQ ID NO: 2) so as to give maximum homology to conserved amino acid residues or nucleotides present in the amino acid sequences or nucleotide sequences. The alignment can be carried out using a known algorism, and a procedure thereof is known to a person skilled in the art. For example, the alignment can be performed by using the Clustal W multiple alignment program (Thompson, J. D. et al, 1994, Nucleic Acids Res., 22: 4673-4680) by default setting. Alternatively, it is also possible to use Clustal W2 and Clustal omega which are revised editions of Clustal W. Clustal W, Clustal W2 and Clustal omega can be used on the website of, for example, European Bioinformatics Institute (EBI [www.ebi-.ac.uk/index.html]) or DNA Data Bank of Japan (DDBJ [www.ddbj.nig.ac.jp/Welcome-j.html]) operated by National institute of Genetics. The position of an amino acid residue or a nucleotide of the target sequence aligned by the alignment to a position corresponding to a certain position on a reference sequence is considered as a "position corresponding to" such a certain position.

As used herein, the "operable linkage" between a control region and a gene means that a gene and a control region are linked to each other in such a manner that the gene can be expressed under control of the control region. A procedure of making the "operable linkage" between a gene and a control region is well known to a person skilled in the art.

The M23A subfamily protease is a protease which has degrading activity on a glycine-glycine bond in a peptide sequence and is classified into an M23A subfamily that is a subfamily of metalloproteases belonging to the M23 family when classified in accordance with the MEROPS database classification method (Rawlings, Neil D., et al. "MEROPS: the database of proteolytic enzymes, their substrates and inhibitors." Nucleic acids research 42.D1 (2013): D503-D509).

As proteases belonging to the M23A subfamily, beta-lytic metallopeptidase (BLP), Las A protein (LasA) (also referred to as staphylolysin), *Aeromonas hydrophila* proteinase (AhP) (also referred to as Mername-AA291 peptidase), BLP homologues derived from *Lysobacter gummosus* (WP_057941690.1) (hereinafter, referred to as LgBLP), BLP homologues derived from *Lysobacter antibioticus*) (WP 057970430.1) (hereinafter, referred to as LaBLP) and the like are known at this time.

Therefore, the proteases belonging to the M23A subfamily in the present invention include BLP, LasA, AhP, LgBLP and LaBLP as well as polypeptides equivalent in functions to these proteases. It is preferable to appropriately select and use one or more of these proteases, and it is more preferable to use BLP or polypeptides equivalent in functions to BLP.

BLP (MEROPS ID: M23.001) is a polypeptide consisting of the amino acid sequence from the amino acid at position 1 to the amino acid at position 179 of SEQ ID NO: 2. Las A (MEROP S ID: M23.002) is a polypeptide consisting of the amino acid sequence from the amino acid at position 1 to the amino acid at position 182 of SEQ ID NO: 4. AhP (MEROPS ID: M23.003) is a polypeptide consisting of the amino acid sequence from the amino acid at position 1 to the amino acid at position 179 of SEQ ID NO: 6. LgBLP is a polypeptide consisting of the amino acid sequence from the amino acid at position 1 to the amino acid at position 178 of SEQ ID NO: 8. LaBLP is a polypeptide consisting of the amino acid sequence from the amino acid at position 1 to the amino acid at position 178 of SEQ ID NO: 10.

Examples of the polypeptide equivalent in functions to BLP, Las A and AhP include polypeptides which consist of an amino acid sequence having an identity of at least 80% to any one of the amino acid sequence from the amino acid at position 1 to the amino acid at position 179 of SEQ ID NO: 2, the amino acid sequence from the amino acid at position 1 to the amino acid at position 182 of SEQ ID NO: 4 and the amino acid sequence from the amino acid at position 1 to the amino acid at position 179 of SEQ ID NO: 6 and which have degrading activity on a glycine-glycine bond in a peptide sequence.

Preferred examples of the polypeptide equivalent in functions to BLP include polypeptides which consist of an amino acid sequence having an identity of at least 80% to the amino acid sequence from the amino acid at position 1 to the amino acid at position 179 of SEQ ID NO: 2 and preferably having His at positions corresponding to positions 22, 121 and 123 and Asp at a position corresponding to position 36 on the amino acid sequence from the amino acid at position 1 to the amino acid at position 179 of SEQ ID NO: 2 and which have degrading activity on a glycine-glycine bond in a peptide sequence.

Preferred examples of the polypeptide equivalent in functions to Las A include polypeptides which consist of an amino acid sequence having an identity of at least 80% to the amino acid sequence from the amino acid at position 1 to the amino acid at position 182 of SEQ ID NO: 4 and preferably having His at positions corresponding to positions 23, 120 and 122 and Asp at a position corresponding to position 36 on the amino acid sequence from the amino acid at position 1 to the amino acid at position 182 of SEQ ID NO: 4 and which have degrading activity on a glycine-glycine bond in a peptide sequence.

Preferred examples of the polypeptide equivalent in functions to AhP include polypeptides which consist of an amino acid sequence having an identity of at least 80% to the amino acid sequence from the amino acid at position 1 to the amino acid at position 179 of SEQ ID NO: 6 and preferably having His at positions corresponding to positions 21, 118 and 120 and Asp at a position corresponding to position 34 on the amino acid sequence from the amino acid at position 1 to the amino acid at position 179 of SEQ ID NO: 6 and which have degrading activity on a glycine-glycine bond in a peptide sequence.

Examples of the polypeptide equivalent in functions to LgBLP include polypeptides which consist of an amino acid sequence having an identity of at least 80% to the amino acid sequence from the amino acid at position 1 to the amino acid at position 178 of SEQ ID NO: 8 and which have degrading activity on a glycine-glycine bond in a peptide sequence.

Examples of the polypeptide equivalent in functions to LaBLP include polypeptides which consist of an amino acid sequence having an identity of at least 80% to the amino acid sequence from the amino acid at position 1 to the amino acid at position 178 of SEQ ID NO: 10 and which have degrading activity on a glycine-glycine bond in a peptide sequence. Whether degrading activity on a glycine-glycine bond is present or not can be determined by, for example, examining degradability of an oligo glycine peptide, a Fret-GGGGG substrate described in Examples, or the like. However, the method for the determination is not limited thereto.

The M23A subfamily proteases described above can be extracted or prepared from microorganisms producing the proteases, or cultures thereof. For example, BLP can be extracted or prepared from *Lysobacter* sp. (NBRC 12725 or NBRC 12726), *Achromobacter lyticus* M497-1, *Lysobacter* sp. IB-9374, *Lysobacter gummosus* DSMZ 6980 or the like, or a culture thereof; LAS can be extracted or prepared from *Pseudomonas aeruginosa* PA01, *Pseudomonas aeruginosa* ATCC 10145, *Pseudomonas aeruginosa* FRD1 or the like, or a culture thereof; and AhP can be extracted or prepared from *Aeromonas hydrophila* subsp. *hydrophila* ATCC 7966, *Aeromonas hydrophila* (Chester) Stanier (ATCC 51307) or the like, or a culture thereof. The above-described microorganisms can be purchased from public microorganism culture collections.

A microorganism producing such an M23A subfamily protease may be cultured under appropriate conditions using a culture medium containing consumable carbon sources, nitrogen sources, metal salts, vitamins and the like. From the thus-obtained microorganism or culture solution, an enzyme can be recovered and prepared by a common method, and subjected to freeze-drying, spray drying, crystallization or the like to obtain the enzyme in a desired form. For example, the enzyme can be collected and prepared from the culture using normal methods such as separation of microorganisms by centrifugation or filtration, precipitation of the enzyme in the supernatant or the filtrate by addition of a salt such as ammonia sulfate or by addition of an organic solvent such as ethanol, concentration or de-salting using an ultrafiltration membrane, and purification by any of various kinds of chromatography such as ion-exchange or gel permeation chromatography.

Alternatively, the M23A subfamily protease can be produced by chemical synthesis or a biological method using the amino acid sequences (SEQ ID NOS: 2, 4 and 6) described above. For example, in accordance with the method disclosed in Patent Literature 3, an M23A subfamily protease can be obtained by culturing *Bacillus* bacteria transformed so as to express a polynucleotide encoding the protein prepared by extracting genomic DNA by a conventional method from a microorganism originally producing a target M23A subfamily protease or extracting RNA to synthesize cDNA by reverse transcription, and then preparing a target enzyme from the culture. Examples of the transformed *Bacillus* bacteria prepared here include *Bacillus* bacteria obtained by introducing M23A subfamily protease genes (SEQ ID NOS: 1, 3 and 5) operably linked to control regions into genomes or plasmids of host cells, and *Bacillus* bacteria containing an expression vector in which a target gene is incorporated at an appropriate position.

Here, the "control region" of a gene is a region which has a function of controlling expression of a gene downstream of the region in cells, and preferably has a function of constitutively expressing or highly expressing the downstream gene. Specifically, the control region can be defined as a region which is present upstream of a coding region in the gene and has a function of controlling transcription of the gene by interaction of RNA polymerases. Preferably, the control region of a gene is a region of about 200 to 600 nucleotides upstream of a coding region in the gene. The control region includes a transcription initiation control region and/or a translation initiation control region of a gene, or a region from the transcription initiation control region up to the translation initiation control region. The transcription initiation control region is a region including a promotor and a transcription initiation point, and the translation initiation control region is a site corresponding to the Shine-Dalgarno (SD) sequence forming a ribosome binding site with an initiation codon (Shine, J., Dalgarno, L., Proc. Natl. Acad. Sci. USA., 1974, 71: 1342-1346).

The expression vector containing an M23A subfamily protease gene can be prepared by incorporating an M23A subfamily protease gene into a vector capable of stably holding the gene, replicating and maintaining the gene in a host microorganism and stably expressing the M23A subfamily protease. Examples of the vector include shuttle vectors such as pHA3040SP64, pHSP64R or pASP64 (JP-B-3492935), pHY300PLK (expression vector capable of transforming both *Escherichia coli.* and *Bacillus subtilis*; Jpn JGenet, 1985, 60: 235-243) and pAC3 (Nucleic Acids Res, 1988, 16: 8732); and plasmids usable for transformation of *Bacillus* bacteria, such as pUB110 (J Bacteriol, 1978, 134: 318-329) and pTA10607 (Plasmid, 1987, 18: 8-15). It is also possible to use plasmids derived from *Escherichia coli.* (e.g. pET22b(+), pBR322, pBR325, pUC57, pUC118, pUC119, pUC18, pUC19 and pBluescript).

Host *Bacillus* bacteria can be transformed using a protoplast method, a competent cell method, an electroporation method or the like. The host *Bacillus* bacterium is preferably *Bacillus subtilis* or a variant strain thereof. Examples thereof include *Bacillus subtilis* strains in which extracellular protease production is decreased while sufficiently keeping the M23A maturing ability.

The resulting transformant may be cultured under appropriate conditions using a culture medium containing consumable carbon sources, nitrogen sources, metal salts, vitamins and the like. From the thus-obtained culture, an enzyme can be recovered and prepared by a common method, and subjected to freeze-drying, spray drying, crystallization or the like to obtain the enzyme in a desired form. For example, the enzyme can be collected and prepared from the culture using normal methods such as separation of recombinant microorganisms by centrifugation or filtration, precipitation of the enzyme in the supernatant or the filtrate by addition of a salt such as ammonia sulfate or by addition of an organic solvent such as ethanol, concentration or de-salting using an ultrafiltration membrane, and purification by any of various kinds of chromatography such as ion-exchange or gel permeation chromatography.

Alternatively, the M23A subfamily protease can be prepared from an enzyme composition containing the M23A subfamily protease, or the like. For example, BLP can be prepared from Achromopeptidase. Achromopeptidase is a bacteriolytic enzyme derived from *Lysobacter enzymogenes*, and contains BLP. Achromopeptidase is commercially available from Wako Pure Chemical Industries, Ltd. etc.

As shown in Examples below, an M23A subfamily protease, e.g. BLP, is equivalent in elastin degrading activity to savinase (S8 family protease) which is a commercially available common bating enzyme and degrades elastin, and it has been shown that BLP can degrade elastin at a deeper part of hide as compared to savinase, and hardly degrades collagen.

Patent Literature 2 indicates that treatment with elastase alone may be effective as a method for degrading elastin while suppressing collagen degradation. However, as shown in Examples, it has been confirmed that even when a purified product of pig pancreas-derived elastase (PPE (Si family protease)) which is one of the most common elastases is used, it is not possible to obtain equivalent elastin selectivity and equivalent degrading activity on elastin at a deep part of leather to those of BLP.

Therefore, the M23A subfamily protease is useful as a leather improving enzyme, preferably a bating enzyme, for suppressing contraction of hide or imparting an area-enlarging effect, and can be a leather improving agent, preferably a bating agent.

In the present invention, the "leather improvement" means that elastin at a deep part of hide is degraded to exhibit a contraction-suppressing effect or an area-enlarging effect on hide. The mode of use of the "leather improving agent" is not limited as long as a contraction-suppressing effect or an area-enlarging effect can be imparted to hide, and the leather improving agent can be used before, after or during any of the steps for leather production, and is preferably used in the bating step.

The bating step means an enzyme treatment step carried out in leather production.

The leather improving agent of the present invention may be an M23A subfamily protease alone, or may be an enzyme composition containing an M23A subfamily protease.

Such an enzyme composition may be a solid composition, for example, in the form of powder, or a liquid composition.

To the enzyme composition containing an M23A subfamily protease, surfactants, chelating agents, water-soluble polymers, water-miscible organic solvents, alkali agents, organic acids or salts thereof, enzymes other than M23A subfamily proteases, enzyme stabilizing agents, antioxidants, solubilizers, pH adjusters, buffering agents, preservatives, perfumes, salts, alcohols, sugars, sawdust, clay and the like can be appropriately added in addition to the M23A subfamily protease.

As the surfactant, any surfactants such as anionic surfactants, nonionic surfactants, cationic surfactants, ampholytic surfactants and gemini surfactants can be used alone, or used in combination of two or more thereof. The content of the surfactants in the enzyme composition is preferably from 0.05 mass % to 20 mass %, more preferably from 0.1 mass % to 10 mass %.

Examples of the nonionic surfactant include polyoxyethylene(polyoxyalkylene)alkyl ethers having a hydrocarbon group having 8 or more and 22 or less carbon atoms, preferably a linear alkyl group having 8 or more and 18 or less carbon atoms, and a polyoxyethylene chain in which ethyleneoxy groups are bonded in an amount of 1 mol or more and 20 mol or less on average, and if necessary, a polyalkyleneoxy chain in which alkyleneoxy groups each selected from the group consisting of a propyleneoxy group and a butyleneoxy group are randomly bonded or block-bonded in an amount of 0 mol or more and 5 mol or less on average to ethyleneoxy groups; polyoxyethylene methyl (or ethyl) ether fatty acid esters obtained by reacting ethylene oxide in an amount of 1 mol or more and 20 mol or less with a methyl- or ethyl-esterified product of a fatty acid having 8 or more and 22 or less carbon atoms; fatty acid alkanolamides in which one fatty acid having 8 or more and 18 or less carbon atoms is amide-bonded to a primary or secondary alkanolamine, where the alkanolamide has, as alkanol groups, one or two alkanol groups each having 2 or 3 carbon atoms, which are bonded to a nitrogen atom and optionally have a polyoxyethylene chain having an average addition molar number of 1 or more and 6 or less, and the alkanolamide optionally has an alkyl group having 1 or more and 3 or less carbon atoms; alkyl (poly)glucosides having a linear or branched hydrocarbon group having 8 or more and 22 or less carbon atoms, preferably a linear alkyl group, where the glucose has an average condensation degree of 1 or more and 3 or less; and glycerol fatty acid ester, pentaerythritol fatty acid esters and sorbitan fatty acid ester which mainly contain a monoester and in which glycerin, pentaerythritol or sorbitan as a polyhydric alcohol is ester-bonded to a fatty acid, and ethylene oxide adducts thereof.

Examples of the anionic surfactant include compounds which have an alkyl group or an alkenyl group having 8 or more and 22 or less carbon atoms and an anionic group and which are any of a linear alkyl benzenesulfonic acid salt, an alkyl or alkenyl sulfuric acid ester salt, a polyoxyethylene (polyoxypropylene)alkyl or alkenyl sulfuric acid ester salt, a polyoxyethylene(polyoxypropylene)alkyl or alkenyl ether carboxylic acid salt, an α-olefin sulfonic acid salt, an internal olefin sulfonic acid salt (including HAS isomers) which is a salt of sulfonated internal olefins having an unsaturated bond at position 2 or higher and preferably position 8 or lower, an α-sulfofatty acid salt, an α-sulfofatty acid methyl ester salt, a fatty acid salt, a phosphoric acid ester salt-based surfactant, an acyl alaninate and an acyl taurate.

Here, examples of the salt include salts with alkali metals, and salts with alkaline earth metals. The salts may be of potassium, sodium, calcium and magnesium, or may be of ammonia or a mono- to trialkanolamine having an alkanol group having 2 or more and 4 or less carbon atoms, preferably monoethanol amine or the like, or a salt may be formed by adding an acid, and neutralized by adding an alkali agent or a strong base-weak acid salt such as sodium carbonate in the system.

Examples of the cationic surfactant include quaternary ammonium salts having 1 or more and 3 or less long-chain alkyl groups or alkenyl groups having 8 or more and 25 or less carbon atoms and optionally interrupted by an ester bond, an ether bond or an amide bond between carbon bonds and short-chain groups each selected from the group consisting of methyl, ethyl and hydroxyethyl as residual groups, with a chlorine ion, a bromine ion, a methyl sulfate ion or an ethyl sulfate ion as a counter ion; tertiary amines having 1 or more and 3 or less long-chain alkyl groups or alkenyl groups optionally interrupted by an ester bond, an ether bond or an amide bond between carbon bonds, and short-chain groups each selected from the group consisting of methyl, ethyl and hydroxyethyl as residual groups, and acid salts thereof; mono-long-chain alkyl or alkenyl trimethyl ammonium salts having an alkyl group or an alkenyl group having 8 or more and 25 or less carbon atoms; di-long-chain alkyl or alkenyl dimethyl ammonium salts; mono-long-chain alkyl or alkenyl pyridinium salts; and mono-long-chain alkyl or alkenyl amide propyl dimethyl amines, or acid salts thereof. Preferred examples include chlorine salts or ethylsulfonic acid salts of alkyl (di- or tri)methyl quaternary ammonium having one or two long-chain alkyl groups having 8 to 22 carbon atoms, chlorine salts or ethylsulfuric acid salts of quaternary ammonium having 1 or more and 3 or less alkanoyl oxyethylene groups having 11 to 25 carbon atoms, and an alkyl group having 1 or 2 carbon atoms, or a hydroxyethyl group; and fatty acid amide propyl dimethyl amines having one long-chain alkyl group having 8 to 22 carbon atoms.

Examples of the ampholytic surfactant include compounds having an alkyl group or an alkenyl group having 8 or more and 22 or less carbon atoms, an anionic group and a cationic group, e.g. ampholytic surfactants of alkyl betaine type, alkyl amide betaine type, imidazoline type, alkyl aminosulfone type, alkyl aminocarboxylic acid type, alkyl amide carboxylic acid type, amide amino acid type or phosphoric acid type, such as alkyl acetic acid betaines, alkanol amide propyl acetic acid betaines, alkyl imidazolines and alkyl alanines. Preferred examples include sulfobetaines or carbobetaines having an alkyl group having 10 to 18 carbon atoms.

Examples of the gemini surfactant, which may be classified as a nonionic surfactant in some cases, include compounds which have a polarity depending on pH and which have an alkyl group or an alkenyl group having 8 or more and 22 or less carbon atoms, and an amine oxide group. Preferred examples include alkylamine oxides having one or two alkyl groups or alkenyl groups having 8 or more and 22 or less carbon atoms, which may be bonded through an amide propylene group to a nitrogen atom forming the amine oxide, and having two alkyl groups having 1 or more and 3 or less carbon atoms, and more preferred examples include alkyl dimethylamine oxides having an alkyl group having 8 or more and 18 or less carbon atoms, and fatty acid amide propyl dimethylamine oxides having a fatty acid residue having 8 or more and 18 or less carbon atoms.

Examples of the chelating agent include amino polyacetic acids such as nitrilotriacetic acid, iminodiacetic acid, ethylenediamineacetic acid, diethylenetriaminepentaacetic acid, glycol ether diaminetetraacetic acid, hydroxyethyliminodiacetic acid, triethylenetetraminehexaacetic acid, djenkolic acid and methylglycinediacetic acid, or salts thereof; organic acids such as diglycolic acid, oxydisuccinic acid, carboxymethyloxysuccinic acid, citric acid, lactic acid, tartaric acid, oxalic acid, malic acid, oxydisuccinic acid, gluconic acid, carboxymethylsuccinic acid and carboxymethyltartaric acid, and salts thereof; aminotri(methylenephosphonic acid), 1-hydroxyethylidene-1,1-diphosphonic acid, ethylenediaminetetra(methylenephosphonic acid) and diethylenetriaminepenta(methylenephosphonic acid), and salts thereof. The salts are as described in the section of anionic surfactants, and may be used as acidic pH adjusters.

The content of the chelating agent in the enzyme composition according to the present invention is preferably from 0.001 mass- to 5 mass %, more preferably from 0.005 mass % to 4 mass %, in terms of an acid type.

Examples of the water-soluble polymer include polymer compounds which having (i) a polyether chain moiety composed of a polymerization unit derived from epoxide having 2 to 5 carbon atoms; and (ii) a polymer chain moiety composed of polymerization units derived from one or more unsaturated carboxylic acids selected from the group consisting of acrylic acid, methacrylic acid and maleic acid, and having a graft structure in which one of (i) and (ii) is a main chain and the other is a branched chain (JP-A-2010-275468 and JP-A-10-060496); and water-soluble polymers having an alkylene terephthalate unit and/or an alkylene isophthalate unit, and an oxyalkylene unit and/or a polyoxyalkylene unit (JP-A-2009-155606).

The content of the water-soluble polymer in the enzyme composition according to the present invention is preferably from 0.01 mass % to 10 mass %, more preferably from 0.05 mass % to 5 mass.

Examples of the water-miscible organic solvent include alkanols, alkylene glycols, glycerin, polyalkylene glycols, (poly)alkylene glycol (mono or di)alkyl ethers, alkyl glyceryl ethers, and aromatic ethers of (poly)alkylene glycol. The alkanol is preferably methanol, ethanol, propanol or the like, the alkylene glycol is ethylene glycol, propylene glycol, butylene glycol, hexylene glycol the like, more preferably ethylene glycol or propylene glycol, even more preferably glycerin, and examples of the polyalkylene glycol is preferably diethylene glycol, triethylene glycol, dipropylene glycol, tripropylene glycol, polyethylene glycol, polypropylene glycol, or polyethylene glycol polypropylene glycol which may be a random or block polymer, more preferably diethylene glycol, dipropylene glycol, polyethylene glycol or polypropylene glycol. The (poly)alkylene glycol (mono or di)alkyl ether is preferably polyoxyethylene monobutyl ether having an average addition molar number of 1 or more and 3 or less, polyoxypropylene monopropyl ether having an average addition molar number of 1 or more and 3 or less, or the like, more preferably diethylene glycol monobutyl ether, and the alkyl glyceryl ether is preferably alkyl (poly) glyceryl ether having an alkyl group having 1 or more and 8 or less carbon atoms, more preferably 2-ethylhexyl glyceryl ether or isoamyl glyceryl ether. The aromatic ether of (poly)alkylene glycol is preferably (poly)oxyethylene monophenyl ether having an average addition molar number of 1 or more and 3 or less, (poly)oxyethylene benzyl ether having an average addition molar number of 1 or more and 3 or less, or the like, more preferably monoethylene glycol monophenyl ether, diethylene glycol monophenyl ether, triethylene glycol ether monophenyl ether, ethylene glycol monobenzyl ether, or diethylene glycol monobenzyl ether.

The content of the water-miscible organic solvent in the enzyme composition according to the present invention is preferably from 0.1 mass % to 40 mass %, more preferably from 0.5 mass % to 35 mass %.

Examples of the alkali agent include inorganic alkali agents such as sodium hydroxide, potassium hydroxide, sodium carbonate and potassium carbonate, and alkanolamines having 1 to 3 C2-C4 alkanols, such as monoethanolamine, diethanolamine, triethanolamine, polyoxyalkyleneamines and dimethylaminopropylamine. Monoethanolamine and triethanolamine are preferable.

The content of the alkali agent in the enzyme composition according to the present invention is preferably from 0 mass to 20 mass %, more preferably from 0 mass % to 10 mass %.

Examples of the organic acid or a salt thereof include the above-described chelating agents, and other organic acids or salts thereof may be used. Examples thereof include polyvalent carboxylic acids such as saturated fatty acids, succinic acid, maleic acid, fumaric acid, and salts thereof; and hydroxycarboxylic acids such as citric acid, malic acid, glycolic acid, p-hydroxybenzoic acid, benzoic acid, and salts thereof.

The content of the organic acid or a salt thereof in the enzyme composition according to the present invention is preferably from 0 mass %, to 5 mass %, more preferably from 0 mass % to 3 mass %.

Examples of enzymes other than M23A subfamily proteases include proteolytic enzymes which are used as common bating enzymes, such as papaya enzyme, subtilisin, and pancreatin which is a crude enzyme extracted from the pancreas of a bovine or a pig.

Examples of the enzyme stabilizing agent include boron compounds, calcium ion sources (calcium ion-supplying compounds), hydroxy compounds and formic acid, examples of the antioxidant include butylhydroxytoluene, distyrenated cresol, sodium sulfite and sodium hydrogen sulfite, and examples of the solubilizers include paratoluenesulfonic acid, cumenesulfonic acid, metaxylenesulfonic acid, and benzoic acid salts (also having an effect as a preservative). Further, the enzyme composition of the present invention may contain paraffins such as octane, decane, dodecane and tridecane, olefins such as decene and dodecene, alkyl halides such as methylene chloride and 1,1,1-trichloroethane, non-water-miscible organic solvents such as terpenes such as D-limonene, dyes, perfumes, antibacterial preservatives, antifoaming agents such as silicone, and the like.

The content of the M23A subfamily protease in the enzyme composition according to the present invention is not particularly limited as long as the protease exhibits activity, and the content is preferably from 0.01 g to 500 g, more preferably from 0.1 g to 200 g, even more preferably from 1 g to 100 g, per kg of the enzyme composition.

In another aspect, the present invention provides a method for treating leather using an M23A subfamily protease. The method includes bringing an M23A subfamily protease or an enzyme composition containing the M23A subfamily protease into contact with hide before, after or during any of the steps for leather production. For example, in one aspect, an M23A subfamily protease or an enzyme composition containing the M23A subfamily protease is brought into contact with limed and delimed hide.

The mode of bringing an M23A subfamily protease into contact with hide may be appropriately selected according to a leather type and region, and the treatment temperature, the treatment time, and the amount of the enzyme used may also be arbitrarily set according to the mode of treatment. For example, a solution containing an M23A subfamily protease or an enzyme composition containing the M23A subfamily protease may be applied to or scattered on the flesh side of hide, and left standing at a temperature of from 15 to 40° C. for a certain amount of time (from 1 hour to 5 hours), or hide may be immersed in such a solution, and left standing at a temperature of from 15 to 40° C. for a certain amount of time (from 1 hour to 5 hours).

Regarding the above-described embodiments, the present invention further discloses the following aspects.

<1> A method for treating leather, comprising a step of bringing an M23A subfamily protease or an enzyme composition comprising the M23A subfamily protease into contact with hide.

<2> The method according to <1>, wherein the M23A subfamily protease is one or more selected from the group consisting of the following a) to e):
  a) a polypeptide consisting of the amino acid sequence from the amino acid at position 1 to the amino acid at position 179 of SEQ ID NO: 2, or a polypeptide which consists of an amino acid sequence having an identity of at least 80% to the amino acid sequence from the amino acid at position 1 to the amino acid at position 179 of SEQ ID NO: 2 and which has degrading activity on a glycine-glycine bond in a peptide sequence;
  b) a polypeptide consisting of the amino acid sequence from the amino acid at position 1 to the amino acid at position 182 of SEQ ID NO: 4, or a polypeptide which consists of an amino acid sequence having an identity of at least 80% to the amino acid sequence from the amino acid at position 1 to the amino acid at position 182 of SEQ ID NO: 4 and which has degrading activity on a glycine-glycine bond in a peptide sequence;
  c) a polypeptide consisting of the amino acid sequence from the amino acid at position 1 to the amino acid at position 179 of SEQ ID NO: 6, or a polypeptide which consists of an amino acid sequence having an identity of at least 80% to the amino acid sequence from the amino acid at position 1 to the amino acid at position 179 of SEQ ID NO: 6 and which has degrading activity on a glycine-glycine bond in a peptide sequence;
  d) a polypeptide consisting of the amino acid sequence from the amino acid at position 1 to 178 of SEQ ID NO: 8, or a polypeptide which consists of an amino acid sequence having an identity of at least 80% to the amino acid sequence from the amino acid at position 1 to the amino acid at position 178 of SEQ ID NO: 8 and which has degrading activity on a glycine-glycine bond in a peptide sequence; and
  e) a polypeptide consisting of the amino acid sequence from the amino acid at position 1 to the amino acid at position 178 of SEQ ID NO: 10, or a polypeptide which consists of an amino acid sequence having an identity of at least 80% to the amino acid sequence from the amino acid at position 1 to the amino acid at position 178 of SEQ ID NO: 10 and which has degrading activity on a glycine-glycine bond in a peptide sequence.

<3> The method according to <2>, wherein the M23A subfamily protease is one or more selected from the group consisting of the polypeptides a), c), d) and e).

<4> A leather improving agent comprising an M23A subfamily protease as an active ingredient.

<5> The leather improving agent according to <4>, wherein the leather improving agent is a bating agent.

<6> The leather improving agent according to <4> or <5>, wherein the M23A subfamily protease is one or more selected from the group consisting of the following a) to e):
  a) a polypeptide consisting of the amino acid sequence from the amino acid at position 1 to the amino acid at position 179 of SEQ ID NO: 2, or a polypeptide which consists of an amino acid sequence having an identity of at least 80% to the amino acid sequence from the amino acid at position 1 to the amino acid at position 179 of SEQ ID NO: 2 and which has degrading activity on a glycine-glycine bond in a peptide sequence;
  b) a polypeptide consisting of the amino acid sequence from the amino acid at position 1 to 182 of SEQ ID NO: 4, or a polypeptide which consists of an amino acid sequence having an identity of at least 80, to the amino acid sequence from the amino acid at position 1 to the amino acid at position 182 of SEQ ID NO: 4 and which has degrading activity on a glycine-glycine bond in a peptide sequence;
  c) a polypeptide consisting of the amino acid sequence from the amino acid at position 1 to 179 of SEQ ID NO: 6, or a polypeptide which consists of an amino acid sequence having an identity of at least 80% to the amino acid sequence from the amino acid at position 1 to the amino acid at position 179 of SEQ ID NO: 6 and which has degrading activity on a glycine-glycine bond in a peptide sequence;
  d) a polypeptide consisting of the amino acid sequence from the amino acid at position 1 to the amino acid at position 178 of SEQ ID NO: 8, or a polypeptide which consists of an amino acid sequence having an identity of at least 80% to the amino acid sequence from the amino acid at position 1 to the amino acid at position 178 of SEQ ID NO: 8 and which has degrading activity on a glycine-glycine bond in a peptide sequence; and
  e) a polypeptide consisting of the amino acid sequence from the amino acid at position 1 to the amino acid at position 178 of SEQ ID NO: 10, or a polypeptide which consists of an amino acid sequence having an identity of at least 80% to the amino acid sequence from the amino acid at position 178 of SEQ ID NO: 10 and which has degrading activity on a glycine-glycine bond in a peptide sequence.

<7> The leather improving agent according to <:6>, wherein the M23A subfamily protease is one or more selected from the group consisting of the polypeptides a), c), d) and e).

<8> Use of an M23A subfamily protease for producing a leather improving agent.

<9> The use according to <8>, wherein the leather improving agent is a bating agent.

<10> Use of an M23A subfamily protease for improving leather.

<11> The use according to any one of <8> and <9>, wherein the M23A subfamily protease is one or more selected from the group consisting of the following a) to e):

a) a polypeptide consisting of the amino acid sequence from the amino acid at position 1 to the amino acid at position 179 of SEQ ID NO: 2, or a polypeptide which consists of an amino acid sequence having an identity of at least 80% to the amino acid sequence from the amino acid at position 1 to the amino acid at position 179 of SEQ ID NO: 2 and which has degrading activity on a glycine-glycine bond in a peptide sequence;

b) a polypeptide consisting of the amino acid sequence from the amino acid at position 1 to the amino acid at position 182 of SEQ ID NO: 4, or a polypeptide which consists of an amino acid sequence having an identity of at least 80% to the amino acid sequence from the amino acid at position 1 to the amino acid at position 182 of SEQ ID NO: 4 and which has degrading activity on a glycine-glycine bond in a peptide sequence;

c) a polypeptide consisting of the amino acid sequence from the amino acid at position 1 to the amino acid at position 179 of SEQ ID NO: 6, or a polypeptide which consists of an amino acid sequence having an identity of at least 80% to the amino acid sequence from the amino acid at position 1 to the amino acid at position 179 of SEQ ID NO: 6 and which has degrading activity on a glycine-glycine bond in a peptide sequence;

d) a polypeptide consisting of the amino acid sequence from the amino acid at position 1 to the amino acid at position 178 of SEQ ID NO: 8, or a polypeptide which consists of an amino acid sequence having an identity of at least 80% to the amino acid sequence from the amino acid at position 1 to the amino acid at position 178 of SEQ ID NO: 8 and which has degrading activity on a glycine-glycine bond in a peptide sequence; and e) a polypeptide consisting of the amino acid sequence from the amino acid at position 1 to the amino acid at position 178 of SEQ ID NO: 10, or a polypeptide which consists of an amino acid sequence having an identity of at least 80% to the amino acid sequence from the amino acid at position 1 to the amino acid at position 178 of SEQ ID NO: 10 and which has degrading activity on a glycine-glycine bond in a peptide sequence.

<12> The use according to <11>, wherein the M23A subfamily protease is one or more selected from the group consisting of the polypeptides a), c), d) and e).

EXAMPLES

Example 1: Preparation of BLP and LgBLP (1-1) Preparation of Transformed Strain

*Bacillus subtilis* 168 strain (*Bacillus subtilis* Marburg No. 168 strain: Nature, 390, 1997, p. 249) was used as a host. The plasmids pHY-BLP2 and pHY-LgBLP disclosed in Patent Literature 4, Example 1 were each introduced by the following method. *Bacillus subtilis* 168 strain was inoculated in 1 mL of LB culture medium, and subjected to shake culturing overnight at 200 rpm at 30° C. 10 μL of the culture solution was inoculated in 1 mL of fresh LB culture medium, and cultured at 200 rpm at 37° C. for 3 hours. This culture solution was centrifuged, and pellets were collected. To the pellets was added 500 μL of SMMP (0.5 M sucrose, 20 mM disodium maleate, 20 mM magnesium chloride hexahydrate salt and 35% (w/v) antibiotic medium 3 (Difco)) containing lysozyme (SIGMA) at 4 mg/mL, and the mixture was incubated at 37° C. for 1 hour. Next, pellets were collected by centrifugation, and suspended in 400 μL of SMMP. 33 μL of the suspension liquid and 20 ng of each plasmid were mixed, 100 μL of 40% PEG was added thereto and stirred, 350 μL of SMMP was further added thereto, and the mixture was then shaken at 30° C. for 1 hour. 200 μL of this liquid was applied to DM3 recycled agar culture medium (0.8% agar (Wako Pure Chemical Industries, Ltd), 0.5% disodium succinate hexahydrate salt, 0.5% casamino acid technical (Difco), 0.5% yeast extract, 0.35% monopotassium phosphate, 0.15% dipotassium phosphate, 0.5% glucose, 0.4% magnesium chloride hexahydrate salt, 0.01% bovine serum albumin (SIGMA), 0.5% carboxymethyl cellulose, 0.005% trypan blue (Merck) and amino acid mixture (tryptophane, lysine and methionine at 10 μL/mL each); % refers to (w/v) %) containing tetracycline (15 μg/mL, SIGMA), and was incubated at 30° C. for 3 days to form a colony.

(1-2) Culture for Enzyme Production

In 1 mL of LB culture medium to which tetracycline had been added to a final concentration of 15 ppm, the recombinant *Bacillus subtilis* colony obtained in (1-1) was inoculated, and then cultured overnight at 150 rpm at 30° C. On the following day, 400 μL of the culture solution was inoculated in 5 mL of 2XL-maltose culture medium (2% tryptone, 1% yeast extract, 1% NaCl, 7.5% maltose, 7.5 ppm manganese sulfate pentahydrate, 21 μM $ZnSO_4$, 15 ppm tetracycline; % refers to (w/v) %), and cultured at 150 rpm at 30° C. for 2 days, and a culture supernatant containing an enzyme produced from bacterial cells was collected by centrifugation.

(1-3) Purification of Enzyme from Culture Supernatant

BLP and LgBLP were each purified from the culture supernatant obtained in (1-2). The culture supernatant was subjected to buffer exchange with 10 mM citric acid-Na pH 6 using Amicon Ultra (molecular weight cutoff 10 K) (Merck Millipore). From the solution after buffer exchange, an enzyme was purified using AKTA explorer 10S (GE Healthcare). The solution obtained by the buffer exchange was caused to pass through TOYOPEARL Gigacap CM-650M Column (TOSOH CORPORATION), and adsorbed components were then eluted using an elution buffer (10 mM citric acid-Na pH 6, 200 mM NaCl). Among the eluted fractions, fraction solutions having degrading activity on FRET-GGGGG (Examples 1 to 4) were collected. Using Amicon Ultra (molecular weight cutoff 10 K), the collected fraction solutions were subjected to buffer exchange with a 20 mM Tris-HCL (pH 7.5) solution to obtain enzyme solutions containing BLP and LgBLP.

(1-4) Measurement of Enzyme Activity

As a substrate, a FRET substrate having pentaglycine between the fluorescence group Nma and the quenching group Lys (Dpn) [hereinafter, FRET-GGGGG] (produced on order in PH Japan Co., Ltd.) was used. Here, Nma refers to 2-(N-methylamino)benzoyl (Nma). Lys (Dpn) refers to a group having 2,4-dinitrophenyl (Dnp) on a side chain of lysine (Lys). To a 96-well black plate, 2 µL of the enzyme solution (appropriately diluted) and 200 µL of 20 mM Tris-HCl (pH 7.5) were added, and 10 µL of a FRET-GGGGG solution (1 mM FRET-GGGGG and 100 mM Tris-HCl (pH 7.5)) was further added to prepare a reaction solution. The fluorescence intensity of the reaction solution was measured with time at a temperature of 30° C., an excitation wavelength of 340 nm and a measurement wavelength of 440 nm using infinite M200 (TECAN). Under the same conditions, the fluorescence intensity of a reaction solution obtained using 20 mM Tris-HCl (pH 7.5) instead of the enzyme solution and equimolar solutions of FRETS-25-STD1 and FRETS-25-STD2 (PEPTIDE INSTITUTE, INC.) instead of FRET-GGGGG was measured to prepare a calibration curve. One unit (U) of activity was an enzyme amount required to change the fluorescence intensity by X/min where X is a fluorescence intensity of a solution containing 1 µmol FRETS-25-STD1 and 1 µmol FRETS-25-STD2. The FRET-GGGGG degrading activity (U/mL) of the enzyme solution was determined.

(1-5) Measurement of Concentration of Enzyme Solution

DC Protein Assay Kit (Bio-Rad) was used for measurement of the concentration of the enzyme solution. BSA Standard Solution (WAKO) was used as a standard solution for calculation of the protein amount.

Example 2: Measurement of Degrading Activity on Elastin and Collagen

BLP, LgBLP, savinase (SIGMA, P3111) and pig pancreas-derived purified elastase (hereinafter, PPE) (Worthington Biochemical, ESFF) were used as proteases. *Bacillus*-derived subtilisin containing savinase is a common bating enzyme (Tanning Chemistry: The Science of Leather).

Bovine neck ligament-derived elastin (SIGMA, E1625) and bovine Achilles tendon-derived collagen (SIGMA, C9879) were used as substrates. To 1 mL of 50 mM Tris-HCl pH 7.5 containing 20 mg of the substrate, each enzyme was added to a final concentration of 1 mg/L. The mixture was reacted at 30° C. for 1 hour, and then centrifuged at 15,000 rpm at 4° C. for 5 minutes, and the supernatant was collected. The amount of peptides in the supernatant was determined using TaKaRa BCA Protein Assay Kit (TaKaRa). An enzyme-free sample was defined as a blank, and the blank value was subtracted to calculate the amount of peptides liberated by protease activity. This amount is defined as degrading activity, and is shown as a relative value to savinase in FIG. 1.

BLP was equivalent in elastin degrading activity to savinase, and had significantly lower collagen degrading activity as compared to savinase. LgBLP had lower elastin degrading activity as compared to savinase, and was as high as BLP in selectivity for elastin. PPE had lower elastin degrading activity and collagen degrading activity as compared to savinase. PPE was equivalent to savinase in selectivity for elastin and collagen.

Example 3: Test on Degradation of Bovine Hide by BLP (3-1) Preparation of Bovine Hide for Bating Lined, dehaired and limed bovine hide was cut to 1.5 cm square and used. Twelve hide pieces were put in a centrifuge tube, immersed in 40 mL of an aqueous ammonium chloride solution containing ammonium chloride at 3% (w/w) of the hide weight, and incubated at room temperature for 60 minutes to perform deliming. The delimed hide pieces were rinsed once with 50 mM Tris-HCl pH 7.5, and used for the following tests.

(3-2) Protease Treatment of Bovine Hide

Two of the hide pieces prepared in (3-1) were put in each screw tube bottle (27 mm×55 mm) containing 5 mL of 50 mM Tris-HCl pH 7.5. To the screw tube bottle, proteases (savinase, PPE and BLP) were added to a final concentration of 50 mg/L to start a reaction. Incubation was performed at 150 rpm at 30° C. for 4 hours, and each hide piece was transferred to 10 mL of 0.1 M sulfuric acid to stop the reaction.

(3-3) Staining of Tissue

A paraffin block was prepared using the protease-treated hide piece obtained in (3-2). The paraffin block was sliced, and an orcein-stained specimen was then prepared, and observed with a microscope. Elastin is stained brown-black in orcein staining. In a sample treated only with a buffer (FIG. 2), a distribution of elastin was observed on the grain side. In a savinase-treated sample (FIG. 3) and a PPE-treated sample (FIG. 4), it was observed that elastin was degraded only at a surface part of the grain side (a dark, solid line that bisects the figure from left to right is drawn on a boundary between the elastin-degraded part and the elastin-remaining part). In a BLP-treated sample (FIG. 5), elastin even at a deep part was degraded, and remaining of elastin under the visual field in FIG. 5 was not observed. FIGS. 2 to 5 each show the images of stained tissues of two hide pieces each independently subjected to protease treatment (right picture and left picture in each figure).

Example 4: Test on Degradation of Bovine Hide by LgBLP

Figure 6:
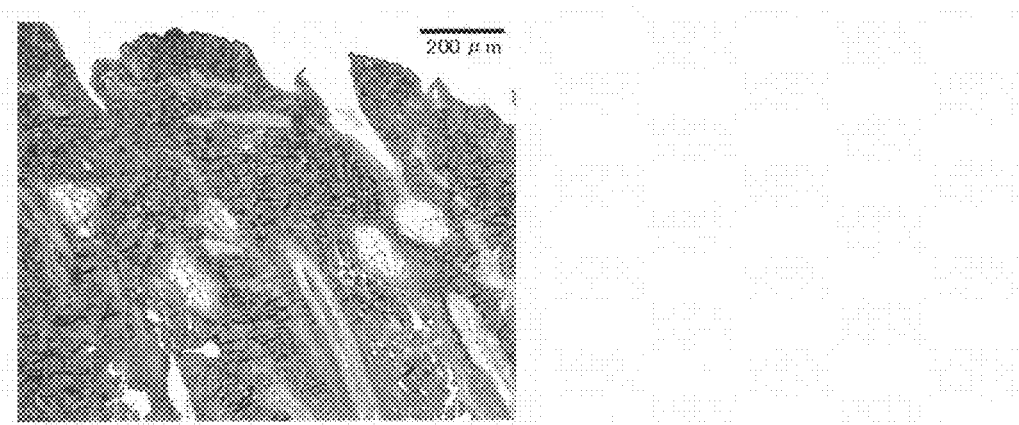
FIG. 6 shows a degrading effect on elastin of bovine hide (without enzyme treatment).
Figure 7:
FIG. 7 shows a degrading effect on elastin of bovine hide (savinase treatment). The dark, solid line that bisects the figure from left to right indicates a boundary between an elastin-degraded part and an elastin-remaining part.
Figure 8:
FIG. 8 shows a degrading effect on elastin of bovine hide (PPE treatment). The dark, solid line that bisects the figure from left to right indicates a boundary between an elastin-degraded part and an elastin-remaining part.
Figure 9:
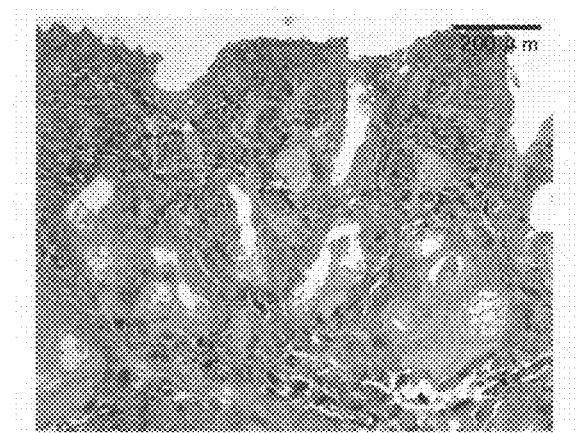
FIG. 9 shows a degrading effect on elastin of bovine hide (LgBLP treatment).

Hide pieces were prepared in the same manner as in (3-1). One of the prepared hide pieces was put in a 12-well microplate to which 2 mL of 50 mM Tris-HCl pH 7.5 was dispensed. Proteases (savinase, PPE and LgBLP) were added to each of the wells to start a reaction. The concentrations of the proteases added were each set to a concentration at which elastin degrading activity equivalent to that of savinase at 50 mg/L was exhibited (calculated from the results of Example 2). Incubation was performed at 150 rpm at 30° C. for 4 hours, and each hide piece was transferred to 10 mL of 0.1 M sulfuric acid to stop the reaction. An orcein-stained specimen was prepared in the same manner as in (3-3), and observed with a microscope. In a sample treated only with a buffer (FIG. 6), a distribution of elastin was observed on the grain side. In a savinase-treated sample (FIG. 7) and a PPE-treated sample (FIG. 8), it was observed that elastin was degraded only at a surface part of the grain side (a dark, solid line that bisects the figure from left to right is drawn on a boundary between the elastin-degraded part and the elastin-remaining part). In a LgBLP-treated sample (FIG. 9), elastin even at a deep part was degraded, and remaining of elastin under the visual field in FIG. 9 was not observed.

The invention claimed is:

1. A method for treating leather, comprising a step of bringing an M23A subfamily protease or an enzyme composition comprising the M23A subfamily protease into contact with hide, wherein the M23A subfamily protease is one or more selected from the group consisting of the following a) to e):
   a) a polypeptide consisting of the amino acid sequence from the amino acid at position 1 to the amino acid at position 179 of SEQ ID NO: 2, or a polypeptide which consists of an amino acid sequence having an identity of at least 80% to the amino acid sequence from the amino acid at position 1 to the amino acid at position 179 of SEQ ID NO: 2 and which has degrading activity on a glycine-glycine bond in a peptide sequence;
   b) a polypeptide consisting of the amino acid sequence from the amino acid at position 1 to the amino acid at position 182 of SEQ ID NO: 4, or a polypeptide which consists of an amino acid sequence having an identity of at least 80% to the amino acid sequence from the amino acid at position 1 to the amino acid at position 182 of SEQ ID NO: 4 and which has degrading activity on a glycine-glycine bond in a peptide sequence;
   c) a polypeptide consisting of the amino acid sequence from the amino acid at position 1 to the amino acid at position 179 of SEQ ID NO: 6, or a polypeptide which consists of an amino acid sequence having an identity of at least 80% to the amino acid sequence from the amino acid at position 1 to the amino acid at position 179 of SEQ ID NO: 6 and which has degrading activity on a glycine-glycine bond in a peptide sequence;
   d) a polypeptide consisting of the amino acid sequence from the amino acid at position 1 to the amino acid at position 178 of SEQ ID NO: 8, or a polypeptide which consists of an amino acid sequence having an identity of at least 80% to the amino acid sequence from the amino acid at position 1 to the amino acid at position 178 of SEQ ID NO: 8 and which has degrading activity on a glycine-glycine bond in a peptide sequence; and
   e) a polypeptide consisting of the amino acid sequence from the amino acid at position 1 to the amino acid at position 178 of SEQ ID NO: 10, or a polypeptide which consists of an amino acid sequence having an identity of at least 80% to the amino acid sequence from the amino acid at position 1 to the amino acid at position 178 of SEQ ID NO: 10 and which has degrading activity on a glycine-glycine bond in a peptide sequence.

2. The method according to claim 1, wherein the M23A subfamily protease is one or more selected from the group consisting of the polypeptides a), c), d) and e).

3. A leather improving agent comprising an M23A subfamily protease as an active ingredient, wherein the M23A subfamily protease is one or more selected from the group consisting of the following a) to e):
   a) a polypeptide consisting of the amino acid sequence from the amino acid at position 1 to the amino acid at position 179 of SEQ ID NO: 2, or a polypeptide which consists of an amino acid sequence having an identity of at least 80% to the amino acid sequence from the amino acid at position 1 to the amino acid at position 179 of SEQ ID NO: 2 and which has degrading activity on a glycine-glycine bond in a peptide sequence;
   b) a polypeptide consisting of the amino acid sequence from the amino acid at position 1 to the amino acid at position 182 of SEQ ID NO: 4, or a polypeptide which consists of an amino acid sequence having an identity of at least 80% to the amino acid sequence from the amino acid at position 1 to the amino acid at position 182 of SEQ ID NO: 4 and which has degrading activity on a glycine-glycine bond in a peptide sequence;
   c) a polypeptide consisting of the amino acid sequence from the amino acid at position 1 to the amino acid at position 179 of SEQ ID NO: 6, or a polypeptide which consists of an amino acid sequence having an identity of at least 80% to the amino acid sequence from the amino acid at position 1 to the amino acid at position 179 of SEQ ID NO: 6 and which has degrading activity on a glycine-glycine bond in a peptide sequence;
   d) a polypeptide consisting of the amino acid sequence from the amino acid at position 1 to the amino acid at position 178 of SEQ ID NO: 8, or a polypeptide which consists of an amino acid sequence having an identity of at least 80% to the amino acid sequence from the amino acid at position 1 to the amino acid at position 178 of SEQ ID NO: 8 and which has degrading activity on a glycine-glycine bond in a peptide sequence; and e) a polypeptide consisting of the amino acid sequence from the amino acid at position 1 to the amino acid at position 178 of SEQ ID NO: 10, or a polypeptide which consists of an amino acid sequence having an identity of at least 80% to the amino acid sequence from the amino acid at position 1 to the amino acid at position 178 of SEQ ID NO: 10 and which has degrading activity on a glycine-glycine bond in a peptide sequence.

4. The leather improving agent according to claim 3, wherein the leather improving agent is a bating agent.

5. The leather improving agent according to claim 3, wherein the M23A subfamily protease is one or more selected from the group consisting of the polypeptides a), c), d) and e).

* * * * *